(12) United States Patent
Horino et al.

(10) Patent No.: US 7,531,184 B2
(45) Date of Patent: May 12, 2009

(54) COMPOSITE POWDERS AND COSMETICS CONTAINING THE SAME

(75) Inventors: Masaakira Horino, Kanagawa (JP); Miwa Ohara, Saitama (JP); Katsuki Ogawa, Kanagawa (JP); Sadaki Takata, Kanagawa (JP)

(73) Assignees: Miyoshi Kasei, Inc., Saitama-shi (JP); Shiseido Company, Ltd., Tokyo (JP)

( * ) Notice: Subject to any disclaimer, the term of this patent is extended or adjusted under 35 U.S.C. 154(b) by 371 days.

(21) Appl. No.: 10/372,669

(22) Filed: Feb. 25, 2003

(65) Prior Publication Data

US 2003/0180535 A1 Sep. 25, 2003

Related U.S. Application Data

(63) Continuation of application No. PCT/JP01/07047, filed on Aug. 15, 2001.

(30) Foreign Application Priority Data

Aug. 31, 2000 (JP) .............................. 2000-263749
Mar. 19, 2001 (JP) .............................. 2001-77992

(51) Int. Cl.
*A61K 8/02* (2006.01)
*A61K 9/14* (2006.01)
*A61K 9/16* (2006.01)

(52) U.S. Cl. ...................... 424/401; 424/489; 424/490
(58) Field of Classification Search ................. 424/489, 424/400, 401, 490, 484
See application file for complete search history.

(56) References Cited

U.S. PATENT DOCUMENTS

| 5,607,504 A | 3/1997 | Schmid et al. |
| 5,628,934 A * | 5/1997 | Ohno et al. ................. 252/586 |

FOREIGN PATENT DOCUMENTS

| EP | 0 982 377 A1 | 3/2000 |
| JP | 43-25644 | 11/1968 |
| JP | 4-330007 | 11/1992 |
| JP | 04-330007 | 11/1992 |
| JP | 08-217635 | 8/1996 |
| JP | 8-217635 | 8/1996 |
| JP | 9-020609 | 1/1997 |
| JP | 09-020609 | 1/1997 |
| JP | 9-020621 | 1/1997 |
| JP | 09-020621 | 1/1997 |
| JP | 09-048716 | 2/1997 |
| JP | 2001-302942 | 10/2001 |

* cited by examiner

*Primary Examiner*—S. Tran
(74) *Attorney, Agent, or Firm*—Westerman, Hattori, Daniels & Adrian, LLP.

(57) ABSTRACT

A composite powder containing a powdery base and aluminum hydroxide adhered to at least a portion of the surface of the base, wherein said adhered aluminum hydroxide in the form of a spherical and net structure is comprised preferably in a large amount. In case of using in powdery cosmetics, this composite powder hides wrinkles, pore openings and hard texture of the skin, and thus maintains the correcting effect of the troubled morphology of the skin. Thus, it exerts excellent effects of imparting natural gloss and color tone to the makeup coating without darkness, being superior in a feeling of "elasticity" and transparency, and the like, compared to the conventional products.

The effect of the above object can be more enhanced by the surface treatment such as a further surface treatment by silicon on the surface of said composite powder.

14 Claims, 6 Drawing Sheets

(×20,000)

(×20,000)

(×50,000)

(×5,000)

COMPOSITE POWDERS AND COSMETICS CONTAINING THE SAME

This application is a continuation of international application PCT/JP01/07047, filed on Aug. 15, 2001.

TECHNICAL FIELD

The present invention relates to novel composite powders, preferably, to novel composite powders comprising aluminum hydroxide of a specific shape adhered to at least a portion of the surface of the base usable for a cosmetic powder (partial coating or full coating), that is, novel composite powders comprising aluminum hydroxide-base complex particles. More specifically, the present invention relates to composite powders which are superior in a correcting effect of the troubled morphology of the skin, such as wrinkles, pore openings, hard texture of the skin, as well as in a feeling of "elasticity" and transparency that are rendered by the natural skin color without affording unnatural texture to the cosmetic film, while also affording more spontaneous color tone and gloss, and further to cosmetics containing the same.

BACKGROUND ART

In adjusting the skin color with the conventional foundation, iron oxide (ferrous oxide) is used. In the case of a thick skin color foundation from wheaten to thick wheaten color or bronze color, a large quantity of iron oxide is used. Brightness or chroma of inorganic pigments, such as red iron oxide or other iron oxides, is intrinsically low. On the other hand, skin color dimness is partially ascribable to shortage in reflected red or yellow light. If a large quantity of iron oxide is used for such skin, there has been found no solution for combating dimness of the skin, such that, if such foundation is applied to the skin, the result has been merely a state of glossless and drab finish.

For preventing skin irregularities, such as pores or small wrinkles, various powders have been proposed by producers of component materials and cosmetics. Examples of such powders include powders with the surface of which fine particles have been deposited, powders having the surface coated with a polymer or an oxide, spherically-shaped organic or inorganic powders, or spherically-shaped powders prepared in the form of multi-layered films, such as silica-titanium oxide-silica films. In order to hide these irregularities, such a method has commonly been used to enhance diffusion characteristics of light on the powder surface. Such method hides color irregularities or surface irregularities to achieve a matted feeling as the texture. However, in this case, powdery finish becomes outstanding to detract from the feeling of unity with the skin such that the feeling of transparence inherent to the skin tends to be lost.

In order to afford gloss, the routine recipe has been to admix pearl pigment with a silver interference color for titanium oxide with a geometrical thickness ranging between 20 to 40 μm. If this pearl pigment is used for the thick skin color from wheaten to thick wheaten color or bronze color, there is produced texture different from the appearance color with the result that the unwholesome finishing feeling is produced. If the pearl pigment is admixed in a necessary quantity to the cosmetics in order to afford gloss to the skin, to coat the skin surface irregularities or pores with the pearl pigment, there is produced penumbra between the skin surface irregularities or the shaded portions of the pores and the surface gloss of the pearl pigment, with the result that the pores or small wrinkles become more visible to detract from the intrinsic makeup effects. Moreover, the pearl pigment is unusually strong in its glaring feeling, due to the lustrous appearance proper to the pearl, thus detracting from the finishing feeling.

In JP Patent Kokai Publication No. JP-A-9-20609, there is proposed such cosmetics in which the outer coating structure of an inorganic metal hydroxide on a clay mineral is one of the following (A), (B), (C) and (D):

(A) a complex material in which a coating structure of the inorganic metal hydroxide coating the surface of the clay mineral forms a honeycomb-like structure on a film formed by ultra-small-sized particles (with the mean particle size ranging between 50 to 250 Å;

(B) a complex material in which the coating structure of the inorganic metal hydroxide coating the surface of the clay mineral is formed by a film of ultra-small-sized particles (with the mean particle size ranging between 50 to 250 Å;

(C) a complex material in which a coating structure of the inorganic metal hydroxide coating the surface of the clay mineral is a hybrid structure made up by a film formed by ultra-fine particles with a mean particle size of 50 to 250 Å and a honeycomb-like structure provided thereon; and (D) a complex material having a structure in which particles with a mean particle size of 0.08 to 0.8 μm are embedded in a coating structure of an inorganic metal hydroxide film of ultra-fine particles, with a mean particle size of 50 to 250 Å, coating the surface of the clay mineral.

If the outermost layer of the coating powders has the honeycomb structure, the ratio of adhesion is satisfactory, because of its ability to entangle with the irregular surface of the skin due to such structure. However, if this honeycomb structure is used in an amount not less than 15 weight % in the cosmetics, the feeling of use, as an essential requirement for cosmetics, is appreciably lowered, while "powdery finish" occurs so that the intrinsic transparency of the skin is lost.

Consequently, there is a demand for such powders which, while having a correcting effect of the troubled morphology of the skin, targeted by the present invention, exhibit natural gloss and color tone and are free from the impression of dimness, and which, while giving the "elasticity" in the cosmetic film, are able to maintain the transparency.

TASK/OBJECT OF THE INVENTION

Under the above-described situation, there is raised a demand for powders having a correcting effect of the troubled morphology of the skin, which hides wrinkles, open pores and hard texture of the skin when used for cosmetics, and in particular, excellent powders in affording "elasticity" to the skin and in transparency by adding natural gloss and maintenance of color tone. In addition, there is raised a demand for powders which should display beautiful makeup effect to cope with variable individual differences, in consideration that the human subject exhibits marked individual differences, such that skin color, for example, ranges from white to wheaten color and thick wheaten color to beige, the skin gloss level differs depending on the skin character which covers the fatty skin, normal skin, fatty dry skin (mixed type skin) and the dry skin gloss level, as a function of age, living environment or diet, and that irregularities on the skin surface differ in magnitude from person to person.

It is an object of the present invention to improve the invention described in the gazette of the aforementioned JP Patent Kokai Publication No. JP-A-9-20609, as proposed by some of the present inventors, and to provide powders which, when used in particular for cosmetics, are able to afford the improved "elasticity" excellent in the "gloss", "color tone" and "correcting effect of the troubled morphology" and further the transparency, in addition to maintaining and further improving the aforementioned correcting effect of the troubled morphology.

DISCLOSURE OF THE INVENTION

The present inventors conducted perseverant researches towards solving the task and achieving the object, and have found that, when powders adhering a large amount of aluminum hydroxide on the surface of particles of a powdery base (usable as cosmetic powders), in particular, powders comprising complex particles of a base and aluminum hydroxide, obtained by adhering aluminum hydroxide (as particle(s)) to at least a portion of the surface of particles so that aluminum hydroxide thus adhered will present a specified shape, are used as cosmetics, the improved "elasticity" and transparency are demonstrated, and that, when the surface of the resulting powders is treated with a surface treating agent, in particular silicone, amino acids, lecithin, fluorine compounds or metal soap, the targeted effect can be improved further. The base may be formed of a singe sort of the material or of complex materials. If the base is formed of the complex material, such a particle (complex particle) comprised of a material for a powder (a powder making up a core of the complex particle) and a coating by another material on an outer side of the particle is desirable. Moreover, such a method has been found in which, by suitably controlling the interference color and the degree of gloss, the skin color and stretching conforming to each subject can be accorded to the skin. The present invention has been completed on the basis of these various findings.

According to the present invention, there is provided a complex particle powder comprising a base for powders usable as cosmetics, which may be of a single sort of material or of a complex material, and aluminum hydroxide adhered to at least a portion of the surface of the base, wherein this aluminum hydroxide forms a specific shape. More specifically, there is provided a specific particle, for example a particle of a base having a specific size, thickness and a refractive index, and aluminum hydroxide adhered with a specific shape to the surface of the base particle and exhibits a desirable refractive index (1.56) and density (2.77 g/cm$^3$), with the composite powder exhibiting a superior effect unprecedented in the related art when the material is used as cosmetics. Such powder is the composite powdered material of the present invention.

Meanwhile, "elasticity" is defined as such a state exhibiting a transparency compared to the ideal or natural bare skin and natural gloss and color tone of the skin (dimness-free bright even skin color) and also not displaying wrinkles and pores. Specifically, such a state in which the color tone is approximate to the natural skin color (skin of babies or that of teens), the pore is hidden and the skin is free from wrinkles is termed "elastic".

Accordingly, the present invention may be summarized as follows:

[1]

The present invention lies in a composite powder comprising a base for powders usable as cosmetics, and aluminum hydroxide adhered to at least a portion of the surface of the base, wherein each powder contains at least 10 weight % (not less than 10 weight %) of the adhered aluminum hydroxide in a total weight of the base and the aluminum hydroxide.

[2]

In a preferred embodiment, the present invention lies in a composite powder containing a powdery base and aluminum hydroxide adhered to at least a portion of the surface of the base, wherein the aluminum hydroxide adhered contains a spherically shaped and a mesh-like formation (consisting of aluminum hydroxide). In a more specific embodiment, the present invention lies in a composite powder containing a powdered base and aluminum hydroxide adhered to at least a portion of the surface of the base, wherein the surface of the aluminum hydroxide has coated with spherically-shaped and mesh-like formations (consisting of aluminum hydroxide) on its surface.

That is, the present invention is characterized in that such specified formation(s) of aluminum hydroxide is contained in the adhered aluminum hydroxide. Such specified formation may be formed as the aluminum hydroxide layer, or the aluminum hydroxide layer may be coated with such formation(s). The adhered aluminum hydroxide may, of course, contain only such specified formation(s) of aluminum hydroxide.

Within the scope not impeding the object or the meritorious effect of the present invention, it is possible to have other components, (such as base components or adhered particulate components), to perform other surface treatment or to provide a further coating. These variations may be comprised within the scope of the present invention.

[3]

For the powdered base, a powder usable for cosmetics may be used to give a composite powder excellent as cosmetics.

The composite powder may be used not only for cosmetics but also for paints, a variety of pigments and the like subject to proper selection of the powdered base.

[4]

The surface formations of the adhered aluminum hydroxide include spherically-shaped formations (spherically-shaped fine particles of aluminum hydroxide). These spherically-shaped formations (spherically-shaped fine particles of aluminum hydroxide may include spheres (spherically-shaped formations), ellipsoids (formations like rugby balls), formations or the formation that may be deemed to be spheres, such as disc-like or spindle-shaped formations. It is possible for these formations to be contacted and/or adhered to one another in the planar and/or vertical direction. More preferably, the surfaces of these spherically-shaped formations are coated with mesh-like aluminum hydroxide. These aluminum hydroxide formations are all included in the aluminum hydroxide adhered to the base surface. A larger quantity of the spherically-shaped and mesh-like formations are preferably formed on the base surface in that it further improves the meritorious effect of the present invention.

[5]

While the above-mentioned various spherically-shaped formations are included in the adhered aluminum hydroxide, these formations may comprise combinations in the planar and/or vertical direction of one or more of these formations.

The planar direction means a direction parallel to the base surface and refers to a state in which plural spherically-shaped formations adhered on the base surface are adhered to one another. The spherically-shaped formations may be adhered together in a straight line or plural spherically-shaped formations may be adhered on a planar surface to one spherically-shaped formation.

The vertical direction means a direction perpendicular to the base surface, and refers to such a state in which spherically-shaped formations are not adhered directly to the base but are adhered on other formations, spherically-shaped or otherwise, that is in which the spherically-shaped formations are adhered indirectly or spatially to the base.

[6]

The mesh-like formations in the adhered aluminum hydroxide may comprise two-dimensionally shaped formations (planar formations) and/or three-dimensionally (sterically) shaped formations.

The two-dimensionally shaped formations mean planar formations, that is, the formations of the usual planar net structure. The totality of the meshes of the planar mesh-like structure may be adhered to the base surface, or only one ends of the formations may be adhered to the base or to the spherically-shaped formations, with the majority of the mesh-like formations then lying along the height-wise direction.

The three-dimensionally shaped formations indicate that plural planes consisting of the net or mesh are adhered together three-dimensionally. The mesh-like formations may, of course, be adhered to the base surface or to the surfaces of the spherically-shaped formations. The mesh-like formations, not directly adhered to these surfaces, may, however, be indirectly or spatially adhered through other mesh-like formations.

[7]

If the composite powder is used for cosmetics, the base usable as cosmetics is selected. With respect to the size of the base, if the base consists of a single material, the average particle size of the particle is about 0.1 to 600 µm, preferably about 0.3 to 500 µm, more preferably about 1 to 400 µm and most preferably about 2 to 100 µm. If the base consists of a complex material, the complex material may contain such a material having the above-mentioned average particle size range and another material having an average particle size of 2 to 500 nm, preferably 5 to 300 nm and more preferably 10 to 200 nm.

If the base consists of a complex material, a particle having a coating of another material (a complex particle) on the outside of one material for powder (a particle of the core of complex particle) is preferable. In this case, the particle size of the particle coated or adhered on the surface of said one material for powder may be preferable about 2 to 500 nm, more preferably 5 to 300 nm, most preferably about 10 to 200 nm.

[8]

There is no particular limitation to the shape of the base. Examples of the base shape include plate shape, flaky shape, bar shape, semi-spherical shape, X-shape, star-shape, flower petal shape, ribbon shape, star-fish shape and a butterfly shape. Of these, the plate shape and the flaky shape are preferred.

Although there is no limitation to the base thickness, the particles of preferably about 0.01 to 10 µm, and more preferably about 0.1 to 6 µm may be used if the base is formed of a sole type of the material. If the base is formed of a complex material, the thickness of the coating layer corresponds to the average particle size of the particles used for coating. This average thickness is preferably about 2 to 500 nm, more preferably about 5 to 300 nm and most preferably about 10 to 200 nm. The layer of the coating particles may be used as it is applied to the surface of for example the surface of the base formed of the sole type material.

[9]

The aforementioned spherically-shaped particles, formed of aluminum hydroxide, may contain spherically-shaped fine particles of aluminum hydroxide with the mean diameter preferably about 0.1 to 10 µm, more preferably about 0.2 to 5 µm and most preferably about 0.3 to 2 µm.

[10]

If the spherically-shaped particles, formed of aluminum hydroxide, are of ellipsoidally-shaped particles, that is particles in the form of rugby balls, the average long diameter may preferably be about 0.4 to 2 µm and more preferably about 0.2 to 1.5 µm, while the average short diameter may preferably be about 0.2 to 1.5 µm and more preferably about 0.1 to 1 µm.

[11]

The length of one unit of the mesh forming the mesh-like formation of adhered aluminum hydroxide, that is the length of one side of a mesh of the mesh-like formation, is preferably about 300 nm or less, while the thickness (diameter) of the particle corresponding to a string forming the mesh is preferably about 5 to 30 nm.

It should be noted that aluminum hydroxide: $Al(OH)_3$ used for adhesion in the present invention includes ball-shaped formations, including spherically-shaped and ellipsoidally-shaped formations, so that, based on these shapes, light scattering effects are effectively displayed. The particle size is increased to inhibit blue to white coloration due to scattering in the Mie area to demonstrate the transparency. By adhering the mesh-like aluminum hydroxide in a ball shape, specifically a spherical or ellipsoidal shape, as the transparency is exhibited, the mesh effect is added to the effect proper to the shape of $Al(OH)_3$, thereby accomplishing the meritorious effect as targeted by the present invention based on the equilibrium with the transparency.

[12]

As for the refractive index of the powders (base) usable as cosmetics forming composite powders, powders with a refractive index preferably about 1.3 to 2, more preferably about 1.4 to 1.8 and most preferably about 1.42 to 1.76 may be used in case the base is formed of a sole type material. If on the other hand the base is a complex material and the above-mentioned coating is to be formed thereon, coated powders obtained on coating the surface of the complex material having the above-mentioned refractive index with powders usable as cosmetics (inorganic substances) having the refractive index preferably about 1.8 to 3, more preferably about 2 to 3 and most preferably about 2.1 to 2.8, may be used.

[13]

As for the amount of adhered aluminum hydroxide, it is possible for the amount of aluminum hydroxide adhered to the composite powders of the present invention to be about 2 to 75 weight %, preferably about 5 to 70 weight %, more preferably about 10 to 60 weight % and still more preferably about 15 to 50 weight % based on the total weight of the base to which aluminum hydroxide is adhered (the entire composite powders), preferably on the total weight of adhered aluminum hydroxide and the base.

[14]

When the base is formed of the single material, the material may preferably be clay mineral, barium sulfate, alumina, silica, magnesium fluoride and hydroxyapatite. One of more of these components may selectively be used. If on the other hand the base is a complex material, at least one of the above-mentioned materials may be used as one of the component materials of the complex material.

[15]

When the base is formed of the complex material, a coating may be applied to the aforementioned powder having the component explained in connection with the case where the base is formed of the single material. The component of the coating may be any of titanium oxide, basic lead carbonate, bismuth oxychloride, cadmium oxide, zirconium oxide, tin oxide, silver and gold. At least one of these substances may be used.

[16]

The resulting product may be surface-treated with a layer of a variety of surface treating agents. As surface treating agents, those used for surface treating the powders of cosmetics may be used. In particular, surface treating layers of silicone, amino acids, lecithin, fluorine compounds or metal soap are desirable. These may also be used in combination.

[17]

The base may be of a plate shape, flaky shape, bar shape, spherical shape, semi-spherical shape, X-shape, butterfly shape, star-shape, flower petal shape, ribbon shape or star-fish shape. Of these, the plate shape and the flaky shape are preferred.

[18]

The cosmetics obtained as described above, in particular those containing the composite powders obtained with use of the base for cosmetics, are comprised in the present invention. In particular, 1 to 100 weight % of the composite powders may preferably be used in the cosmetics.

Other necessary components may also be used depending on the type, dosage form or object of the cosmetics, so that powders or composite powders so far commonly used may naturally be used.

Preferably, composite powders may be used in an amount of about 1 to 80 weight % in case of a solid powder cosmetics (powdery cosmetics), about 1 to 30 weight % in case of emulsified cosmetics, and about 0.5 to 50 weight % in case of non-aqueous cosmetics (mixture of wax and oil or a mixture thereof with resin), respectively.

EMBODIMENTS OF THE INVENTION

Figure 1:
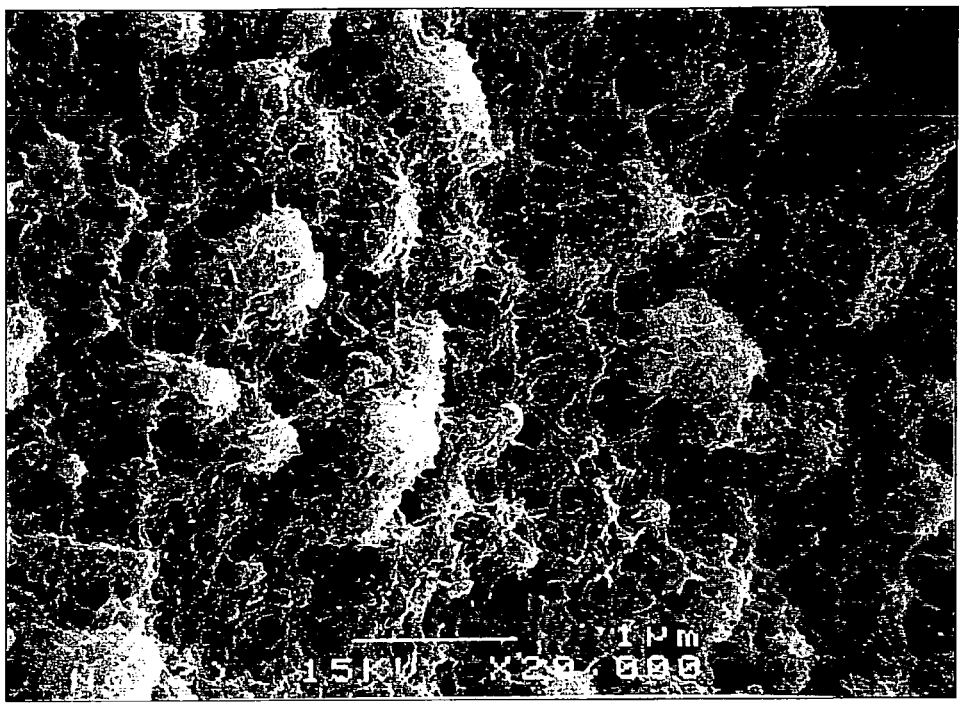
FIG. 1 shows a SEM photograph (magnification factor: 20,000) of composite powders, produced in Example 1, and to which aluminum hydroxide is adhered.

In the following, preferred embodiments of the present invention are explained in detail. It should be noted that, although the following explanation is to be centered about certain preferred embodiments of the invention, the scope of the present invention encompasses but is not limited to the contents of these preferred forms.

In the present invention, a base or a substrate forming the composite powders has a mean particle size about preferably 0.1 to 600 μm in mean particle size, (as measured by a device employing the laser diffraction method, manufactured by HORIBA SEISAKUSHO), with the average thickness of the base preferably being about 0.01 to 10 μm (as measured by the method of encapsulating the base with a resin and observing its segmented piece with TEM). The refractive index of the base, as used in the present invention, is preferably about 1.3 to 2, more preferably about 1.4 to 1.8, and most preferably about 1.42 to 1.76, whilst its mean particle size is more preferably about 0.3 to 500 μm and further more preferably about 1 to 400 μm.

If a single material is used as the base, it may be composed of, for example, clay mineral, barium sulfate, alumina, silica, magnesium fluoride and hydroxyapatite.

Preferred examples of the clay mineral include illite groups such, as sericite (silky mica), muscovite, biotite, lithia mica, and synthetic mica, and kaolin groups such as kaolionite, nacrite, dekkite, halloysite, and, sillimanite groups such as sillimanite and kyanite, and magnesium silicate systems such as talc, and serpentine groups.

When a complex material is used as the base used in the present invention, composite powders as powders of the aforementioned single material, in particular the powders of a component with the refractive index ranging between 1.3 and 2, such as a material comprised of at least one of clay mineral, barium sulfate, alumina, silica, magnesium fluoride and hydroxyapatite, and powders of another material, namely one or more of titanium oxide, basic lead carbonate, bismuth oxychloride, cadmium oxide, zirconium oxide, tin oxide, silver or gold, may be used.

It is particularly preferred to use a complex material comprised of a powder of the component used as the single material and a coating formed of the component of the aforementioned other material, which coating is formed on the surface of the aforementioned powder.

If the complex material is used as the base, the complex material used may be pearl pigments, iris foliate pearl pigments or colored pigments, having interference colors, such as gold, red, orange, green, blue or purple color, hard capsules, such as titanium oxide encapsulating silica, zinc oxide encapsulating silica, PMMA-titanium oxide or PMMA-silica, multi-layered film powders, such as silica-titanium oxide-silica, silica-cerium oxide-silica, starchy polyethylene powders, silica-nylon powders or zinc oxide-sericite. For demonstrating the effect of the present invention more efficiently, iris foliate pearl pigments or colored pearl pigments are particularly preferred.

Other more preferred examples of the base (complex material) used in the present invention include a composition comprised of powders of variable shapes as described above and titanium oxide coated to a geometrical thickness on the surface of the powders, such as titanium-mica, a composition comprised of powders of the variable shapes as described above and titanium oxide coated to a geometrical thickness on the surfaces of the powders, and lower titanium oxide coated on the so coated powders as necessary, and a composition comprised of powders of the variable shapes, titanium oxide coated to a geometrical thickness on the surfaces of the powders, and a color tint affording component, such as iron black, further adhered to the titanium oxide coating.

The complex material of the present invention may also be constituted by bonding fine particles of metal hydroxides or metal oxides to the surface of the powder forming the base of variable shape, coating titanium oxide on the resulting powder surface to a geometrical thickness, further coating the resulting powder surface with lower titanium oxide as necessary or bonding iron black to the powder surface. Such bonding of the coating further reinforces the color tone of the interference color and elevates the force of natural coverage while improving the morphological correcting effect, color tone correcting effect, tightness of contact, feeling of transparency and bare skin feeling.

As a method for acquiring the pearl gloss and various interference colors, by forming a layer of titanium oxide on the surface of the powder having various shapes, a vacuum deposition processing method may be used. In actuality, however, such a method may be used which consists in hydrolyzing an aqueous solution of an inorganic acid salt of titanium, for example, titanyl chloride, in the presence of powders of variable shapes, precipitating a hydrous titanium oxide on the surface of the powders of variable shapes and subsequently heating the resulting powder, as exemplified by the Du Pont's method (see JP Patent Kokoku JP-B-43-25644).

The so generated complex material (base) presents various interference colors, depending on the thickness of the titanium coating layer on the surface of the powder having variable shapes. If the amount of titanium oxide is 10 to 25 weight % based on the weight of the product (based on the total weight of the powder and titanium oxide), the interference color is usually silver. If the amount is 25 to 40 weight %, the interference color is gold. If the amount is 40 to 50 weight %, the interference color is continuously changed from red, blue and green, in this order, as the amount of the layer of the titanium oxide is increased. If the amount of titanium oxide is 50 to 60 weight %, the interference color is gold of higher order and the like.

| (interference color) | range of geometrical thickness of $TiO_2$ (m$\mu$) |
| --- | --- |
| silver | 20 to 40 |
| gold | 40 to 90 |
| red | 90 to 110 |
| indigo | 110 to 120 |
| blue | 120 to 135 |
| green | 135 to 155 |
| gold of second order | 155 to 175 |
| indigo of second order | 175 to 200 |

In this manner, in case of applying a coating of titanium oxide, the desired color tone can be selected within the range of the geometrical thickness about 20 to 200 m$\mu$ (millimicron). The component of the coating may preferably be oxides of titanium, as described above, or oxides of bismuth, zinc, cadmium, zirconium or tin. Since the interference color differs a trifling with various coating components, the geometrical thickness of the coating may be suitably selected depending on the coating component used. The aforementioned change in the color tone (interference color) may usually be found for the range of the desirable geometrical thickness about 40 to 200 m$\mu$ (millimicron).

As for the pearl pigment comprised of natural mica, on the surface of which titanium oxide and iron oxide (ferrous oxide) are coated in this order, such a product has been marketed in which the coverage of the titanium oxide is 15 to 48 weight %, the coverage of iron oxide is 5 to 26 weight % and the particle size distribution is about 5 to 100 μm. For example, the following products are being marketed and can be used as the base in the present invention.

| coverage of titanium oxide (%) | particle size (μ) | coverage of iron oxide (%) | pearl gloss |
| --- | --- | --- | --- |
| 48 | 5 to 25 | 10 | moderate reddish gold |
| 23 | 10 to 60 | 22 | reddish thick gold |
| 16 | 10 to 60 | 24 | reddish gold |
| 36 | 10 to 60 | 8 | slightly bluish gold |

It has already been known to blend various pearl pigments (flaky pearl pigments) in conventional foundations. These pearl pigments present unusually strong glaring, due to gloss proper to pearl, to deteriorate the finish or to render pores and small wrinkles more visible.

If conversely the complex material is used as the base and spherically or ellipsoidally shaped aluminum hydroxide is coated with netted aluminum hydroxide, the "elastic" feeling can be imparted to the skin. That is, the transparency may be demonstrated on the cosmeticized skin to a bright uniform skin color with more spontaneous color tone suited to the skin of the particular user without drabess in addition to demonstrating the correcting effect of the troubled morphology of the skin, such that the improved "elasticity" can be afforded to the skin along with the transparency in a manner free from gloss peculiar to pearl and from unnatural texture feeling.

The interference color may be controlled by the geometrical thickness of the titanium oxide layer of the titanium mica pearl pigment to realize various color tones. It has also been found that the color tone of the interference color in the pearl pigment can be changed by adjusting the amount of adhesion of aluminum hydroxide according to the present invention. Specifically, if the coating is such that the quantity of aluminum hydroxide is about 10 to 15 weight % based on the total weight of the base prior to adhesion of aluminum hydroxide, there may be obtained a marked effect of changing the color phase as the pearl gloss is reduced moderately, whereas, if the quantity of aluminum hydroxide exceeds 15 weight %, the correcting effect of the troubled morphology is demonstrated in preference to the effect of changing the color phase or the natural gloss, while saturation tends to be lowered. It has also been found that this change in the color phase coincides with the direction of change of the geometrical thickness of titanium oxide and that of change of the interference color, with the thickness of aluminum hydroxide demonstrating the effect of further changing the color tint of the interference color.

As the base used in the present invention, powders of a light transmitting inorganic substance of low refractive index, having various shapes, may be used. In this case, the refractive index is low and is preferably 1.3 to 2, more preferably 1.4 to 1.8 and most preferably 1.42 to 1.76. This range of the refractive index may be applied both to the refractive index of the single material of the base, when the base is formed of such single material, and to the refractive index of an intermediate component material, both surfaces of which are to be coated, in case the base is formed of the complex material having the intermediate component material.

In the case of the complex material, it is sufficient if the refractive index of the coating is selected to be larger than that of a component material, provided inwardly of the coating, for example, a powdered component of an inorganic substance, and may, for example, be about 1.8 to 3, more preferably about 1.8 to 2.8 and most preferably about 2.1 to 2.8. As for the difference between the refractive index of the coating and that of the inner powdered component, a difference about not less than 0.3 and preferably about 0.5 to 1.4 may be selected.

Turning to the density of the powders of the light-transmitting inorganic substance used for the base, and density of the coating, the density of the powders of the light-transmitting inorganic substance is preferably in a range from 1.9 to 5.5. In case the base is a complex material, the density of the coating is preferably in a range from 3.5 to 8.2. Preferably, the density of the coating is to be higher than the density of the powdered inorganic substances used on the inner side.

The following shows concrete examples of the powdered light-transmitting inorganic substances and the coating that can be used as ingredients of the base in the present invention. The components of the powders and the coating, exemplified in the following Table, are naturally the components that may be used in the present invention. Even if not shown here as examples, those components having the properties substantially equivalent to these components may be used in the present invention, and thus encompassed in the scope of the invention.

| (Powders of the inorganic substances) | | |
| --- | --- | --- |
| powdered inorganic substance | refractive index (n) | density (p) |
| magnesium fluoride | 1.378 | 3.148 |
| silica (SiO$_2$) | 1.42 | 2.2 |
| zeolite | 1.47 | 2.15 |
| montmorrilonite | 1.52 | 2.5 |
| kaolin | 1.56 | 2.58 |
| sericite | 1.57 | 2.8 |
| talc | 1.58 | 2.7 |
| mica | 1.59 | 2.8 |
| diatomaceous earth | 1.46 | 2.0 |
| magnesium oxide | 1.74 | 3.65 |
| barium sulfate | 1.62 | 4.47 |
| dolomite | 1.68 | 2.9 |
| alumina | 1.76 | 3.95 |
| roseki | 1.6 | 2.9 |
| yttria | 1.92 | 5.03 |
| zinc oxide | 2.0 | 5.5 |

| (Coating) | | |
| --- | --- | --- |
| coating | refractive index (n) | density (p) |
| titanium oxide (R) | 2.71 | 4.2 |
| titanium oxide (A) | 2.52 | 3.5 |
| basic lead carbonate | 1.9 | 6.4 |
| bismuth oxychloride | 2.15 | 7.7 |
| cadmium oxide | 2.49 | 8.15 |
| zirconium oxide | 2.20 | 5.49 |
| tin oxide | 1.99 | 6.95 |
| gold | 3.0 | |
| silver | 3.0 | |

If titanium oxide coats the surface of a powder having variable shapes, to provide a titanium oxide coated mica (complex material), added to with lower titanium oxide, the amounts thereof may be varied over a wide extent. For example, the amount of titanium oxide based on 100 parts by weight of the crude powder material prior to being coated with titanium oxide is about 20 to 150 parts by weight and more preferably about 29 to 150 parts by weight, while lower titanium oxide, used as necessary for coating, may preferably be about 0.01 to 60 parts by weight and more preferably about 1 to 10 parts by weight. If the amount of lower titanium oxide is less than 0.01 weight % based on the powder material having a particular shape, the resulting composite powder material tends to be inferior in the power of generation of interference color. If the amount of lower titanium oxide exceeds 60 weight %, not only is the intensity of the interference color apparently changed in intensity, but also the composite powder material undesirably becomes brittle or the cohesion of particles becomes stronger, depending on the type of the powders used.

By preparing the present base as the geometrical thickness of the layer of the particles of titanium oxide coated on the powder surface, and by forming the composite powder material of the present invention, using this base, it is possible to create various soft pliable touch feeling, force of natural coverage and bright transparent color tone. For example, the novel composite powders, with the blue to purple interference color, affords the force of natural coverage and transparency to the skin, while the novel composite powders, with the greenish interference color, affords the force of natural coverage, while suppressing a transparent reddish color feeling to the skin, without providing a dark cosmetic film. The composite powders with the yellow to reddish color affords a bright skin color, the force of natural coverage and a transparent healthy feeling, through a cosmetic film, and is capable of hiding variations in skin color and skin surface irregularities to make the skin to appear uniform.

The particles of aluminum hydroxide, used in a structure of a base usable for cosmetics used in the present invention, is preferably crystalline because of numerous points of diffusion within a lattice, even granting that these particles may be amorphous. The refractive index of these particles of aluminum hydroxide is 1.56.

The proportion and the quantity of use of adhered aluminum hydroxide depends on the sort of the base usable in the cosmetics used in the present invention, or on the average particle size or on the various surface properties of the base. Specifically, the quantity of aluminum hydroxide used may be 2 to 75 weight %, preferably 5 to 70 weight %, more preferably 10 to 60 weight % and most preferably 15 to 50 weight %, based on the total weight of the base usable in cosmetics, to which aluminum hydroxide is adhered, that is on the total weight of the entire composite powders, particularly preferably on the sum of the amounts of the base and aluminum hydroxide. If the amount of aluminum hydroxide is excessive, the amount of scattered reflected light is increased, thus the feeling of transparence being lost to give whitish makeup finishing. In particular, if iris foliate pearl pigment is used, the color effect proper to the iris foliate pearl pigment is undesirably diminished such that the meritorious effect targeted in the present invention is not achieved. If conversely the amount of aluminum hydroxide is too small, the effect of color transition is hardly presented, while the glaring gloss feeling proper to the pearl pigment tends to become outstanding to render the skin surface irregularities, pores, or wrinkles visible to detract undesirably from the makeup effect.

If the base is the complex material, the complex material in its entirety, including e.g., the coating, is equivalent to the base, so that this complex material in its entirety is to be included in the base in making the calculations. Moreover, if aluminum hydroxide is used in the base, aluminum hydroxide is also to be included in the base in making the calculations.

As for aluminum hydroxide for forming a particular shape of the surface of the base, as used in the present invention, aluminum hydroxide, with a mesh-like shape, coated on a spherically or ellipsoidally shaped surface, is preferred. By the particles of aluminum hydroxide, adhered to the powder surfaces, it is possible to construct complex particles, comprised of adhered aluminum hydroxide of the specified shape. Composite powders based on a single material, made up by these particles (mica-Al(OH)$_3$), and composite powders based on a complex material (such as TiO$_2$-mica)-Al(OH)$_3$), are encompassed in the composite powders of the present invention. The shape or the manner of adhesion of shaped structures by the aluminum hydroxide particles may be adjusted to the particular shape or structure of the present invention, depending on the reaction temperature and time in manufacture, pH values, cooling conditions, amounts of water, delicate differences in the surface configuration of the base used or on the difference in the degree of surface activation of aluminum hydroxide generated.

As for the specific shape afforded by the particles adhered and the shape or manner of adhesion of these specifically shaped formations to the base, aluminum hydroxide powders are adhered to the surface of the particles of the base forming the composite powders to form specified shape (by aluminum hydroxide), with aluminum hydroxide of this specified shape forming the complex particles adhered. The powders containing these particles are preferred as the powdered material for cosmetics. The powdered material at least containing these composite powders constitute the composite powders of the present invention. Of course, the composite powders of the present invention may be constituted in their entirety by these complex particles. As for the aforementioned particular shape, constituted by the aluminum hydroxide particles adhered, mesh-like aluminum hydroxide may be adhered in a coating fashion on the surface of a sphere (including an ellipsoidal sphere and a disc-shaped sphere). The degree of the shape structure may be optionally varied depending on the difference of the skin, skin properties, or the skin condition (degree of morphological trouble) of a user being cosmeticized.

The "sphere" or "spherical" in the present invention means not only the shape of a true sphere but also the shape approximate to a sphere, such as an ellipsoidal sphere (like a rugby ball) or a disc-shaped sphere.

(Manufacture of Composite Powders)

In the manufacture of the composite powders of the present invention, no particular difficulties are met, such that the composite powders of the present invention can be manufactured extremely readily by having reference to the disclosure of the present specification, in particular the embodiments which will be shown below. However, certain supplementary explanation is made as follows:

3 to 15 fold amount (by weight) of purified water, based on the amount of the base used, is used. Approximately 2 to 75 weight % of aluminum salts for the manufacture of aluminum hydroxide, based on the total weight of the composite powders inclusive of the base, calculated as aluminum hydroxide, is used. A liquid dispersion, obtained on dissolving aluminum salts in purified water and uniformly dispersing the base therein, is heated to approximately 50 to 100° C. To this liquid dispersion are added seed crystals and the resulting product is agitated and subsequently cooled to approximately 40 to −10° C. The aqueous solution is filtered, washed with water and subsequently dried to give composite powders of the base to which aluminum hydroxide has been adhered.

When the base, to which aluminum hydroxide is adhered, is to be processed with silicone surface treatment, it may be performed by any known method, such as a method disclosed in JP Patent Kokai Publication No. JP-A-9-48716.

(Surface Treatment)

The composite powders obtained in accordance with the present invention helps improve long-lasting properties of make-up, afford moisture retention and moisture-absorbing properties, protect the skin, ameliorate bonding to the skin, adjust the amount of oil absorption, and suppress the desiccation and dry feeling of the skin without loading the skin. The composite powders obtained in accordance with the present invention is preferably surface-processed in order to improve feeling, such as lubricity, extension or moist feeling or dispersion of powders and pigments.

As the surface treatment method, any known routine method may be used, such as treating with lecithin, amino acid, acylglutamic acid, metal soap, fatty acids, fluorine, silicone, moisturizers, polyethylene, or with N-mono long-chain aliphatic acyl basic amino acid (with e.g., 8 to 22 carbon atoms). Such surface treatment may, of course, be carried out by an optional combination of the above treatments. Of these treatments, processing with silicone, amino acids, lecithin, fluorine, lecithin-silicone and with fatty acid-silicone are preferred because of superior effects produced.

There is no particular limitation to the silicone oils used provided that the silicon oils used are those used for ordinary cosmetics. Examples of the silicone oils include dimethyl polysiloxane, cyclic dimethyl polysiloxane, methylphenyl polysiloxane methyl hydrogen polysiloxane, cyclic methyl hydrogen polysiloxane, polyether modified silicone, alkyl modified silicone, methyl polysiloxane emulsion, higher fatty acid ester modified silicone, higher alkoxy modified silicone, and phenol modified silicone.

In metal soap treatment, fatty acid metal salts are preferably used. These fatty acid metal salts with 12 to 18 carbon atoms are particularly preferred. For example, calcium salts, magnesium salts, zinc salts or aluminum salts are preferred. It should be noted that selection of the surface treating agents depends on the dosage type or objectives of use of cosmetics and hence may preferably be made depending on the objectives of use.

In treating with amino acids, the amino acids used are those derived from plants or animals.

In treating with lecithin, lecithin extracted from soybeans or egg yolk is used.

In treating with fluorine, fluorine compounds, such as perfluoroalkyl silane, perfluoroether, perfluoroalkyl phosophoric acid esters or diethanol amine salts of perfluoroalkyl phosphate, may be used.

(Cosmetics)

The composite powders of the present invention, including aforementioned coated composite powders and powders treated with the surface treating agents, such as silicone, may be admixed in the cosmetics. In such case, there is no particular limitation to the amount of use (amount to be admixed) of the composite powders in the cosmetics. In the case of powdery cosmetics, the composite powders of the present invention may be used in an amount preferably of 1 to 100 weight % in a total weight of the composition in its entirety. In the case of caked or kneaded cosmetics, the composite powders of the present invention may be admixed in an amount preferably of 1 to 100 weight %, and more preferably of 1 to 80 weight % in a total weight of the powders to be admixed. In the case of emulsified cosmetics, the composite powders of the present invention are used in an amount preferably of 1 to 60 weight % and more preferably of 1 to 30 weight % based on the weight of the emulsified product in its entirety, whereas, in the case of the non-aqueous cosmetics, the composite powders of the present invention may be used in an amount preferably of 0.5 to 50 weight % and more preferably of 1 to 30 weight %. The composite powders of the present invention can conveniently be mixed in particular into makeup cosmetics, such as foundation, face powders, solid face powders, eye shadow, brusher, nail color, lipstick, or skin care, such as under make-up base, carmine lotion, cream, emulsion or face lotion.

The cosmetics containing the composite powders of the present invention can be admixed with ingredients commonly used in ordinary cosmetics, such as, for example, various oils, surfactants, water-soluble polymers, other powders, moisturizers, antiseptics, drugs, UV absorbers, dyes, inorganic salts, organic acid salts, perfumes, chelating agents, pH controllers, or water, as necessary, in addition to the aforementioned components of the composite powders of the present invention, insofar as the commonly used ingredients used do not detract from the meritorious effect of the cosmetics in the present invention. In similar manner, commonly used ingredients may be suitably used when the composite powders of the present invention are used in paints.

Thus, it is sufficient if the aforementioned composite powders are used as at least effective components when the composite powders of the present invention are used in cosmetics or paints. In addition, commonly used powders, and other components, may be used as an admixture insofar as it does not detract from the features of the present invention.

The aforementioned oils may be oils commonly used for cosmetics, enumerated by, for examples, fluid paraffin, vaseline, paraffin wax, squalane, bees wax, carnauba wax, olive oil, lanoline, higher alcohols, higher fatty acids, ester oils, ceresine, micro-crystalline wax, candellila wax, diglyceride, triglyceride, silicone oil, perfluoropolyether, perfluorodecalin, decalin, perfluorooctane, hohoba oil, octyldodecyl myritinate, or neopentylglycole dioctanoate.

Among the surfactants that can be used, there are non-ionic surfactants, such as polyoxyethylene alkylether, polyoxyethylene fatty acid esters, polyoxyethylene sorbitan fatty acid esters, glycerol fatty acid esters, polyglycerol fatty acid esters, polyoxyethylene glycerol fatty acid esters, polyoxyethylene cured castor oil, or polyoxyethylene sorbitol fatty acid esters, anionic surfactants, reprented by fatty acid soap, such as sodium stearate or palmitic acid triethanolamine, and surfactants commonly used in cosmetics, such as cationic surfactants or amphoteric surfactants.

Among the aforementioned water-soluble polymers, that can be used, there are water-soluble polymers, commonly used for cosmetics, such as carboxymethyl cellulose, methyl cellulose, hydroxyl methylcellulose, polyvinyl alcohol, polyvinyl pyrrolidone, tragacanth gum, carageenan, locust bean gum, dextrin, dextrin fatty acid esters, carboxy vinyl polymer, xanthane gum, gelatin, sodium alginate, or Arabian rubber.

The composite powders, employing a sole substance as the base (single material (base)-Al(OH)3) or the composite powders employing a complex substance as the base (complex substance (base)-Al(OH)$_3$), are powders which, when used in particular as cosmetics, exhibit form correction effect, and which can be used for acquiring a glossy feeling and feeling of transparence, in addition to the feeling of improved 'tensile strength' without affording unnatural texture feeling to the cosmetic film. Moreover, the powders that have so far been used for an object other than the above-mentioned object may similarly be used for routine purposes, such as for thinning the colored pigments with white face powders with a small covering force for using at a moderate concentration for adjusting the coloring power, or adjusting the touch feeling. Among the other powders, used for the routine purposes, there are, for example, inorganic powders, such as talc, mica, kaolin, sericite, muscovite, synthetic mica, bronze mica, lepidolite, biotite, Lithia mica, vermiculite, magnesium carbonate, diatomaceous earth, magnesium silicate, calcium silicate, aluminum silicate, barium silicate, strontium silicate, metal salt of tungstic acid, hydroxyapatite, hydrous silicic acod, magnesium oxide, bentonite, zeolite, ceramics powders, or aluminum hydroxide, organic powders, such as nylon powders, polyethylene powders, polymethyl benzoguanamine powders, polymethyl methacrylate powders, ethylene tetrafluoride powders, microcrystalline cellulose, rice starch, or lauroyl lysine, powders of fatty acid metal salts, such as powders of calcium stearate, zinc stearate, magnesium stearate, magnesium myrostate, cetyl phosphate calcium, or cetyl phosphate zinc sodium, inorganic colored powders, such as toitanium oxide, zinc oxide, zirconium oxide, iron oxide (red iron oxide), iron titanate, iron hydroxide, loess, black iron oxide, carbon black, mango violet, cobalt violet, chromium oxide, chromium hydroxide, cobalt titanium, ultramarine or Prussian blue pearl pigments, such as titanium oxide coating mica, titanium oxide coating bismuth oxychloride, bismuth oxychloride, titanium oxide coating talc, fish scale foil, or colored titanium oxide coating mica, powders commonly used in cosmetics, including metal powders, such as aluminum powders, stainless steel powders or copper powders, and the aforementioned powders processed with silicone oil or fluorine compounds (fluorine processing).

Examples of the aforementioned moisuturizers that can be used include those commonly used for cosmetics, such as sorbitol, xylitol, glycerol, multitol, propylene glycol, 1,3-butylene glycol, 1,4-bytylene glycol, pyrrolidone sodium carboxylate, lactic acid, sodium lactate or polyethylene glycol.

As the aforementioned antiseptics, those commonly used for cosmetics, such as paraoxybenzoic acid alkylesters, sodium benzoate, or potassium sorbate, may be used.

As the drugs, that can be used, there are, for example, those drugs commonly used for cosmetics, such as vitamins, crude drugs, anti-inflammatory agents, or bactericidal agents.

As the UV absorbers, that can be used, there are, for example, those UV absorbers commonly used for cosmetics, such as para-amino benzoinc acid based UV absorbers, anthranyl-based UV absorbers, salicylic acid based UV absorbers, cinnamic acid based UV absorbers, or benzophenone-based UV absorbers.

Among the dyes, that can be used, there are those dyes commonly used for cosmetics, for example, tar dyes, such as Red 104, Red 106, Red 201, Red 202, Red 204, Red 205, Red 220, Red 226, Red 227, Red 228, Red 230, Red 401, Red 505, Yellow 4, Yellow 5, Yellow 202, Yellow 203, Yellow 204, Yellow 401, Blue 1, Blue 2, Blue 201, Blue 404, Green 3, Green 201, Green 204, Green 205, Orange 201, Orange 203, Orange 204, Orange 206, Orange 207, and natural dyes, such as carminic acid, laccaic acid, brazilin, or crocin.

There is no limitation to the form or type of cosmetics in the present invention such that the composite powders may be used for any cosmetics currently available and which may be developed and marketed in future. These cosmetics types may be exemplified by face powders, such as powder foundation, compact powders, two-way cakes, face powders, sweat-controlling powders, or deodorant powders, point makeup agents, such as eye-shadows, powder brushers, masukara, lipsticks, lip gloss, eyebrow pencil, eye liner or nail color, emulsion or non-emulsion products, such as liquid foundation, cream foundation, under-makeup base, solid emulsion type foundations or oily foundation, partial basic cosmetics, such as packs, face lotions, cosmetic liquids, hair care agents, hair tonics, or hairdressing agents, and whole-body products, such as baby powders, body powders, or fragrance powders.

In similar manner, the composite powders of the present invention may be used as a paint, such that use of the composite powders for all forms of the paint may be promising.

Turning to the mechanism of action, there is such a method known in the art to make wrinkles less visible, in which the base surface is fixed with a polymer resin and light diffusion and reflection effects are afforded by the micro-irregularities on the polymer surface to render the wrinkles less visible. Another known method is to approximate the powder to a butterfly in appearance and to exploit its complicated shape to produce diffusion and scattering effects. Both of thee methods utilize the light scattering effect on the article surface. It is a marked feature of the present invention to make selective use of aluminum hydroxide particles having specified refractive index (1.56) on the base surface, with the particles being formed to the aforementioned specified shape and being adhered to the base in a specified structure. While the present invention exploits the light reflecting effect by the spherical shape, inclusive of ellipsoidal shape, of the particles adhered to the base and by the mesh-like aluminum hydroxide layer on the adhered particles, this aluminum hydroxide is a low refractive index substance having a value of the refractive index (1.56) close to the refractive index (1.55) of the corneum of the human being. The morphological trouble correcting effect is determined by the balanced state of the specified shape and structure on one hand and the substance (Al(OH)$_3$). The present invention contemplates to optionally change the amount of adhesion of aluminum hydroxide, which becomes adhered at the specified structure, and the specified shape, to cope with the degree or types of skin troubles which may be variable from one user to another.

The conventional makeup cosmetics use a large quantity of iron oxide to develop a wheaten color through dense wheaten color to bronze skin color, so that the skin color tends to be glossless and dim to dark color. On the other hand, if silver to white pearl color is applied to give gloss, the color tint is distinct from the skin color to give an unhealthy and heterogeneous textural feeling to detract appreciably from the make-up effect. The present invention affixes the aluminum hydroxide of the aforementioned specified shape in a specified structure to the surface of, for example, iris foliate pearl pigment to decrease the conventional peculiar glaring gloss which may render the form trouble more apparent. Apart from this, the present invention uses adhered aluminum hydroxide of a specified shape and structure in an amount of 10 to 15% to produce changes in the color hue of the interference (transition of color phase). The direction of such transition is from yellow to reddish, from reddish to red purple, from blue purple to blue tint and from green to yellow green, this transition coinciding with the change direction of the geometrical thickness and the interference color of titanium oxide. That is, the direction of transition is in the same direction as the change from gold through red, indigo, blue, and green to gold brought about with increasing geometrical thickness of the titanium oxide layer. Thus, 10 to 15 weight % of aluminum hydroxide of the present invention is adhered to thereby delicately change the geometrical thickness to contribute to the change in the color phase. Moreover, the reflected light is of the color hue corresponding to the interference color and is a soft color hue which does not appear to be dim or dark.

The transition of color changes is now scrutinized.

In the case of the pearl pigment, the interference color is changed from silver through gold, red, indigo and blue, in this order, to green, as indicated above. If the thickness is increased, the interference color is weaker, however, it is changed from gold through red, indigo and blue, in this order, to green, as the second order. If the thickness is increased still further, the interference color becomes white color.

If, for the interference color, up to 15 weight % of aluminum hydroxide is adhered to the surface of the pearl pigment, the geometrical thickness is a thickness between red and indigo. This phenomenon can be understood readily. On the other hand, if the amount of aluminum hydroxide is increased, the color change should be from indigo through blue to green, however, the color tone is changed towards non-saturation (white). The primary possible reason is that, judging from the past process of the investigations in this field, the surface of aluminum hydroxide can hardly be uniform or smooth even though the geometrical thickness can be increased. That is, in the context of the present invention, the surface of aluminum hydroxide cannot be maintained microscopically uniform or smooth but presents micro-sized irregularities. It is presumably these micro-sized irregularities that bring about the light scattering effect.

Second, a question arises as to whether or not aluminum hydroxide forms a truly transparent layer. As compared to the refractive index of magnesium fluoride or silica of low refractive index values, the refractive index of 1.56 of aluminum hydroxide is slightly higher. This means that the adhered aluminum hydroxide layer may actually be thought of as being a semi-transparent layer. If the assumption that the aluminum hydroxide layer is semi-transparent is relied upon, this layer undergoes internal light scattering, even if such scattering is not significant.

Third, the thicker the coating layer (the layers of titanium oxide and aluminum hydroxide), the more significant becomes the phase difference scattering, which phase difference scattering is also thought to be a contributing factor.

That is, when the amount of adhesion of aluminum hydroxide is up to 10 to 20 weight %, the surface is microscopically kept smooth and suffers from the effect of phase difference scattering only to a lesser extent, with the effect of the refractive index of aluminum hydroxide of the specified shape being only small and with the amount of adhered aluminum hydroxide being balanced with that of aluminum hydroxide of the specified shape. The result is that the novel composite powders of the present invention, employing the pearl pigment, is particularly excellent in equilibrium between the feeling of transparency, color tone, and gloss on one hand and the morphological trouble correcting effect, thus affording the "elasticity" of the skin.

When the amount of adhesion of aluminum hydroxide of a specific shape and a specific structure exceeds 25%, not only is the phase difference scattering increased due to manifestation of microscopic irregularities on the surface of the novel composite powders or to the increased thickness of the coating layer (of titanium oxide and aluminum hydroxide) but also the light scattering effect is increased due to the increased refractive index proper to aluminum hydroxide, thus further increasing the morphological trouble correcting effect.

As compared to the subject of the JP Patent kokai Publication No. JP-A-9-20609, the composite powders of the present invention evidently has a smoother use feeling. In the subject disclosed in the JP Patent Kokai Publication No. JP-A-9-20609, the outermost layer of the coating powders has a honeycomb structure, with the surface of the structure presenting significant micro-sized irregularities. The result is that, if the powders are coated separately, the powders lack in extension due to the interaction with the micro-sized irregularities of the skin, thus excessively loading the skin. This state is aggravated by the fact that the outermost layer is the non-uniform surface of micro-sized irregularities and that the ultra-micro-sized particles are of higher specific surface. Thus, the powders exhibit marked tendency to adsorb oil and moisture on the skin with the result that the powders are low in extension to give rise to dull use feeling. The feeling of 'high tensile strength' is a compound term in the field of cosmetics having main factors of the morphological correcting effect (the effect of making wrinkles less visible), color tone (the color tone exempt from dimness and being bright and uniform) and natural gloss, seasoned with a feeling of transparence. With the subject of the JP Patent Kokai Publication No. JP-A-9-20609, the same spectroscopic characteristics (gloss) as those of the human skin are exhibited along with the morphological correcting effect. However, the base is the clayey core and white in color so that the feeling of 'high tensile strength' is not demonstrated. Moreover, since it is the scattering effect due to the honeycomb structure that is targeted, the tendency is towards non-saturation, such that no effect of high 'tensile strength' can be exhibited.

The present invention is directed to composite powders containing the base and aluminum hydroxide attached thereto and hence to composite powders adhered with the specific shape and specific structure. Preferably, mesh-like aluminum hydroxide is adhered to the base or to the surface of aluminum hydroxide particles of the spherical shape inclusive of ellipsoidal shape. Also preferably, a larger quantity of the so adhered aluminum hydroxide particles is present on the base surface. The height of the so adhered aluminum hydroxide particles is adjusted to an approximately constant value, with the majority of the aluminum hydroxide remaining adhered in this manner. Although the height of aluminum hydroxide adhered appears slightly different when it is observed by SEM (magnification factor: 20,000), it may macroscopically be deemed to be approximately constant. As may be understood on observation with a SEM, it is the surface of a sphere (including that of an ellipsoid) that is in contact with the skin, and aluminum hydroxide having a microscopically meshed formation is adhered to this surface, so that the number of contact points with the skin is small to give smooth use feeling. Moreover, since microscopically meshed structure of $Al(OH)_3$ improves its adhesion to the skin, it may be understood that this mechanism assures optimum adhesion to the skin to give smooth use feeling.

There is no limitation to the form of the cosmetics according to the present invention. For example, cosmetics according to the present invention may be used in, for example, powders, cakes, pencils, sticks, pellets, ointments, liquids, emulsions or creams. According to the present invention, the composite powders are particularly useful as cosmetics especially for composite powders employing mica as the base. In addition, the composite powders may also be used as various components, including additives for paints, plastics or rubber, mold release agents or lubricants for rubber. Thus, the composite powders represent industrially highly useful products which may also be extensively used in other than the field of cosmetics.

EXAMPLES

The present invention will now be explained with reference to Examples and Comparative Examples, only by way of illustration. Meanwhile, the "parts" denote weight parts, unless specified otherwise.

Example 1

Adhesion of Aluminum Hydroxide to Titanium Mica Surface 21.3 g of sodium aluminate were dissolved in 400 ml of purified water. To the resulting solution were added 100 g of an iris foliate pearl pigment, manufactured and sold by Merck Japan under the trade name of "Iriodin 211 Rutile Fine Red". The resulting mixture was heated to 85° C. under agitation and dispersion. When the temperature of 85° C. was reached, 70.766 g of a liquid dispersion, obtained on dispersing 0.176 g of aluminum hydroxide of 0.08 μm in purified water were added and agitated for five minutes. After the end of the agitation, the resulting liquid dispersion was cooled with water to 60° C. and further quenched in ice to 20° C. The resulting liquid dispersion was continued to be agitated for six hours at a temperature not higher than 20° C. The filtration and washing with water were repeated and, after drying and crushing, red to purple iris foliate pearl pigment, with aluminum hydroxide adhered thereto, was prepared.

Figure 2:
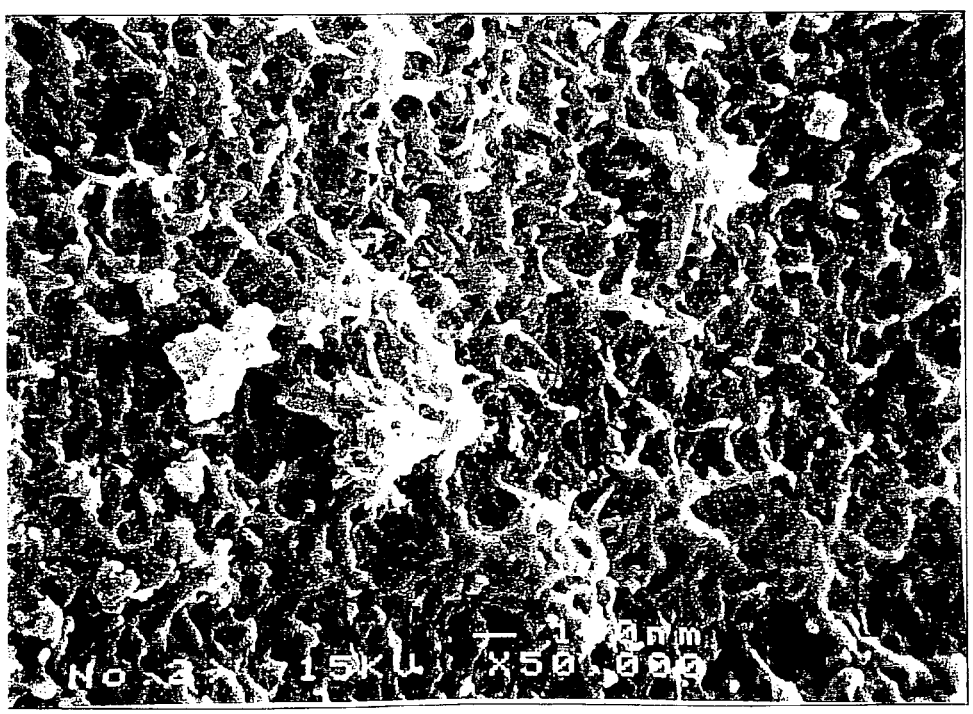
FIG. 2 shows a SEM photograph (magnification factor: 50,000) of composite powders, produced in Example 1, and to which aluminum hydroxide is adhered.

111.7 g of composite powders, comprised of mesh-like aluminum hydroxide adhered to the surface of aluminum hydroxide, attached to the surface of titanium mica, and which were in the form of spheres with a diameter of 0.8 μm or ellipsoids with a long diameter of 0.63 μm and with a small diameter of 0.4 μm, were obtained. A SEM photograph of composite powders, containing 15 weight % of $Al(OH)_3$ adhered thereto (×20,000) is shown in FIG. 1, while another SEM photograph, taken under the same conditions (×50,000) is shown in FIG. 2.

As may be seen from these figures, the mesh-like aluminum hydroxide is adhered to the spherical or ellipsoidal surface of the majority of adhered particles, with the height of the mesh-like aluminum hydroxide being macroscopically uniform.

Comparative Example 1

Composite Powders Disclosed in JP Patent Kokai Publication No. JP-A-9-20609

To 2000 ml of purified water were added 400 g of aluminum sulfate and dissolved. To the resulting solution were added 200 g of muscovite and dispersed uniformly. To this liquid dispersion were added 457 g of urea and processed at 95° C. for 6 hours, cooled, washed with water and ethanol, in this order, and dried at 70° C. to produce aluminum hydroxide coated powders.

Figure 3:
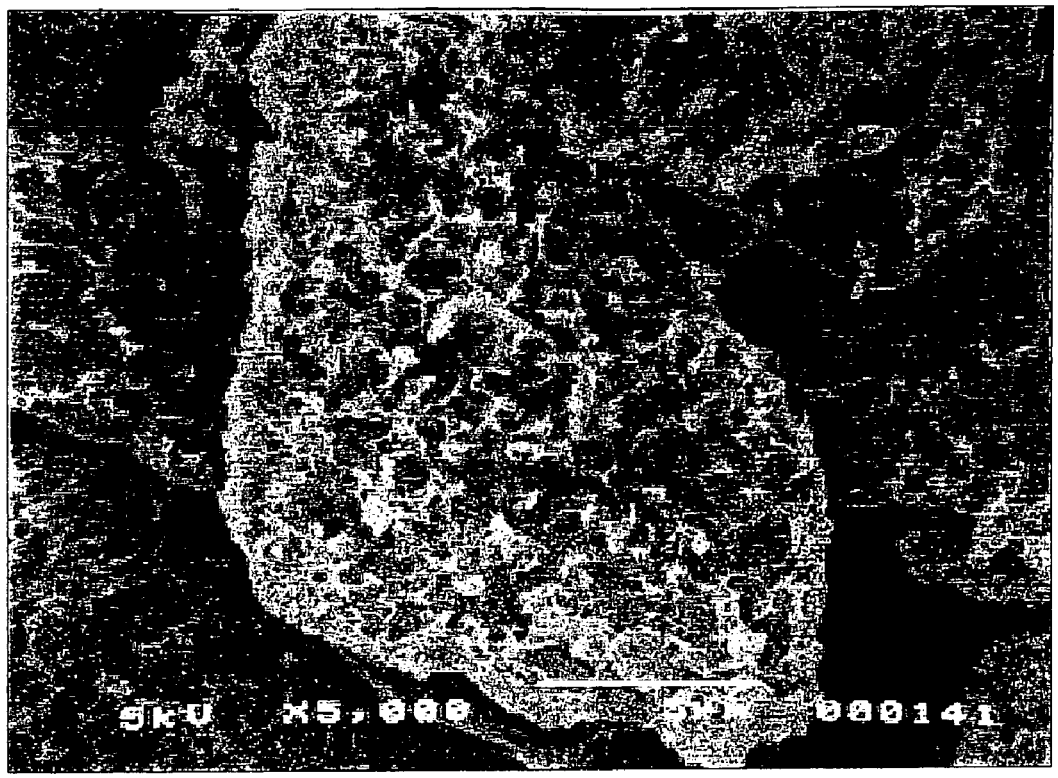
FIG. 3 shows a SEM photograph (magnification factor: 5,000) of aluminum hydroxide coated powders, obtained in Comparative Example 1.

FIG. 3 shows a SEM photograph of the produced coated powders (×5000). It may be seen from this figure that the surface of the powder particle presents a honeycomb shape having significant micro-sized irregularities.

The dynamic frictional coefficient was measured by a friction feeling tester (manufactured by Kato-Tech Co. Ltd.). It was seen from the measured results that the dynamic frictional coefficient shown in the JP Patent Kokai Publication No. JP-A-9-20609 was $3.35 \times 10^{-1}$ MIU, while that of the inventive product is $2.94 \times 10^{-1}$ MIU. The results of comparison indicate that the inventive product is superior in smoothness.

Example 2

Coating of Titanium Oxide to Spherical Alumina and Spherical Magnesium Silicate and Adhesion of Aluminum Hydroxide 50 parts of spherical alumina (mean particle size: 8.3 μm) and 50 parts of spherical magnesium silicate (mean particle size: 9.2 μm) were added to 1,000 parts of purified water and dispersed uniformly. To the resulting liquid dispersion were added 625 parts of a 40 weight % aqueous solution of titanyl sulfate and the resulting product was boiled for eight hours under agitation. After cooling, filtration and washing with water, the resulting product was sintered at 900° C. to produce titanium oxide coated spherical alumina and titanium oxide coated spherical magnesium silicate.

The procedure of Example 1 was repeated except that 100 g of the complex material (powders) obtained as described above were used in place of the irs foliate pearl pigment used in Example 1 to produce a green pearl pigment comprised of aluminum hydroxide attached to the surface of the titanium oxide coating on the spherical alumina and spherical magnesium silicate.

Example 3

Adhesion of Aluminum Hydroxide to the Surface of a Titanium Mica Mixed System 350 ml of purified water was heated to 85° C. and added to with 40.26 g of sodium aluminate. The resulting product was heated to 90° C. When the temperature of 90° C. was reached, 50 g of iris foliate pearl pigment (manufactured by Merck Japan under the trade name of Tymiron Super-Red) and 50 g of iris foliate pearl pigment (manufactured by Merck Japan under the trade name of Tymiron Super-Orange), totaling at 100 g, were added and dispersed uniformly. To the resulting uniform dispersion were added 30 g of a supernatant liquid of a liquid dispersion, obtained on dispersing aluminum hydroxide to the above-mentioned uniform dispersion, that is 1.5% aluminum hydroxide (a supernatant liquid of a liquid dispersion composed of 98.5 ml of purified water and 1.5 g of aluminum hydroxide) and the resulting product was agitated for ten minutes. After cooling to 60° C. with cool water, the resulting product was agitated for eight hours at lower than 20° C. under further cooling with ice water. The resulting product then as repeatedly filtered, washed with water, dried and crushed to prepare a skin color iris foliate pearl pigment to which aluminum hydroxide was adhered.

Example 4

Adhesion of Iron Black and Aluminum Hydroxide to the Surface of the Iris Foliate Pearl Pigment 50 g of iris foliate pearl pigment, manufactured by Merck Japan under the trade name of Tymiron Super-Blue, and 50 g of iris foliate pearl pigment (manufactured by Merck Japan under the trade name of Tymiron Super-Green), totaling at 100 g, were agitated with 1,000 parts of purified water and uniformly dispersed. Into this liquid dispersion was injected a nitrogen gas to purge air off. The resulting liquid dispersion was super-heated under agitation to 80° C. and 20% of ammoniac water was dripped to for adjusting the pH value to 10. The nitrogen gas injection was then discontinued and a solution composed of 13.1 parts of potassium nitrate, 54 parts of ferrous sulfate and 0.6 part of concentrated sulfuric acid dissolved in 1,000 parts of purified water was gradually added dropwise. The dripping amount of 20% ammoniac water was adjusted so that the pH value will be maintained in a range of 9 to 11. The reaction temperature was kept at 80° C. and the agitation speed was kept constant. After the end of the reaction, the resulting product was filtered, washed with water and dried at 100° C. to prepare a blue to green iris foliate pearl pigment.

The procedure of Example 1 was followed except that 100 g of the so produced blue to green iris foliate pearl pigment were used in place of 100 g of the iris foliate pearl pigment used in Example 1 to produce the blue to green iris foliate pearl pigment to which was adhered aluminum hydroxide.

Example 5

Adhesion of Aluminum Hydroxide to the Surface of Colored Titanium Mica Surface

The procedure of Example 1 was followed 1 except that 100 g of the iris foliate pearl pigment, comprised of natural mica, on the surface of which 48% of titanium dioxide and 10% iron oxide were coated (manufactured by Merck Japan under the trade name of Iriodin 302 Gold Satin) were used in place of 100 g of iris foliate pearl pigment used in Example 1. An iron oxide coated pearl pigment, to which moderate red to gold aluminum hydroxide was adhered, could be produced.

Example 6

Preparation of Lipstick

A lipstick was prepared based on the following composition of the lipstick:

| | Composition of lipstick | |
|---|---|---|
| | components | weight parts |
| oil phase | microcrystalline wax | 12.0 |
| | polyethylene wax | 2.8 |
| | rice bran wax | 4.1 |
| | carnaba wax | 0.5 |
| | squalane | 5.1 |
| | cetyl octanoate | 12.8 |
| | tri-2-glycerol ethyl hexanoate | 16.5 |
| | liquid lanoline | 17.3 |
| | cholestryl hydroxystearate | 4.1 |
| | sucrose acetic acid iisolactic acid ester | 3.7 |
| | rose hip oil | 0.5 |
| | 2-ethylhexyl paradimethyl amino benzoate | 2.9 |
| | 4-tert-butyl-4'-methoxybenzoylmethane | 0.5 |
| | d-δ-tocopherol | 0.2 |
| | Glycerol | 1.9 |
| | Purified water | 1.7 |
| | crystalline cellulose | 1.3 |
| pigment | titanium mica-aluminum hydroxide complex (Example 1) | 8.5 |
| | iron oxide | 3.1 |
| | Red 226 | 0.3 |
| | Red 202 | 0.1 |
| | iron black | 0.1 |

(Manufacturing Method)

The entire oil phase components were put into a kiln for dissolution for completely dissolving and dispersing the mixture. To the resulting product, the entire pigment components were added and mixed uniformly. The resulting product was cooled and taken out so as to be then rolled three times. The rolled product was again restored to the kiln for dissolution and dissolved at 85° C. and defoamed. The resulting product was put into a metal mold for lipstick. After cooling, the product was put into a container to prepare a lipstick product.

Example 7

Manufacture of Cream Foundation

A cream foundation was prepared based on the following composition:

| | Composition of cream foundation | |
|---|---|---|
| | components | weight parts |
| oil phase | stearic acid | 1.75 |
| | glycerol monostearate | 3.0 |
| | polyethyleneglycol monostearate | 0.5 |
| | polyoxyethylene sorbitan monostearate | 1.5 |
| | glycerol tri-2-ethyl hexanoate | 3.0 |
| | butylparaben | 0.1 |
| | dibutylhydroxytoluene | 0.05 |

-continued

Composition of cream foundation

| | components | weight parts |
|---|---|---|
| | 2-ethyl hexyl para-dimethyl amino benzoate | 0.2 |
| | cetyl octanoate | 8.2 |
| | squalane | 2.0 |
| | sorbitan sesquioleate | 0.3 |
| | titanium dioxide | 5.0 |
| | skin color iris pearl pigment-aluminum hydroxide complex material (Example 3) | 5.5 |
| Water phase | glycerol | 5.0 |
| | propylene glycol | 5.0 |
| | carboxy methyl cellulose sodium | 0.1 |
| | xanthane gum | 0.05 |
| | methylparaben | 0.3 |
| | triethanolamine | 0.7 |
| | magnesium aluminum silicate | 1.0 |
| | purified water | 56.75 |

(Manufacturing Method)

A mixture of oil phase components was heated to 85° C. for dissolution and dispersion. An entire mixture of aqueous phase components, separately prepared on heating to 85° C., was added to the mixture of the oil phase components, and the resulting mass was emulsified at 85° C. At a time point when the emulsion was finished, the resulting emulsified product was agitated for ten minutes and, after cooling to 30° C., was put into a container to produce a cream foundation.

Example 8

Manufacture of Powder Foundation

Based on the following composition of components, a powder foundation was prepared:

Composition of powder foundation

| | components | weight parts |
|---|---|---|
| powders | silicone processed sericite | 15.0 |
| | amino acid processed sericite | 5.0 |
| | lecithin processed sericite | 5.0 |
| | plate-like barium sulfate | 4.0 |
| | titanium dioxide | 3.0 |
| | polystyrene beads | 6.0 |
| | silica beads | 5.0 |
| | talc | 31.0 |
| | complex material of Example 3 | 8.0 |
| | Complex material of Example 5 | 4.0 |
| oil phase | dimethyl polysiloxane | 7.0 |
| | squalane | 2.0 |
| | cetyl alcohol | 3.0 |
| | hohoba oil | 2.0 |

(Manufacturing Method)

The entire components of the powders were mixed in a Henschel mixer and pulverized by a comminuting device. The resulting powders were transferred to the Henschel mixer which was then heated to 70° C. to adjust the temperature of the powders to approximately 65° C. To these powders was added the total mixture of the oil phase components, which were separately heated and dissolved, and the resulting product was agitated for eight minutes. The resulting agitated product was cooled to 40° C. and taken out. The so produced product was pulverized by the comminuting device and molded to prepare a powder foundation (product).

Comparative Example 2

A powder foundation was prepared in accordance with Example 8, except that, on the surface of 8.0 g of an iris foliate pearl pigment (more precisely, 4.0 g of Tymiron Super-Red and 4.0 g of Tymiron Super-Orange, both being products manufactured by Merck Japan), and of natural mica were coated 48% of titanium dioxide and 10% of iron oxide (ferrous oxide) to give an iris foliate pearl pigment, originally manufactured by Merck Japan under the trade name of "Iriodin 302 Gold Satin", which was usedan an amount of 4.0 g in place of the composite powders of Examples 3 and 5 prepared in Example 8.

Example 9

Manufacture of Caked Eye Shadow

Based on the composition of components, shown below, a caked eye shadow was prepared:

Composition of Caked eye shadow

| | components | weight parts |
|---|---|---|
| powsers | amino acid processed sericite | 6.0 |
| | lecithin processed talc | 20.0 |
| | complex material of Example 5 | 2.0 |
| | complex material of Example 5 | 6.0 |
| | complex material of Example 5 | 18.0 |
| | complex material of Example 5 | 8.0 |
| | iron black | 4.0 |
| | polystyrene beads | 6.0 |
| | Ne-lauroyl-L-lysin | 7.0 |
| | silica beads | 7.0 |
| | methylparaben | 0.2 |
| Oil phase | dimethyl polysiloxane | 5.0 |
| | cetyl octanoate | 1.0 |
| | cctyldodecyl ercate | 5.7 |
| | triglycerol 2-tri-ethylhexanoate | 4.0 |
| | d-δ-tocopherol | 0.1 |

(Manufacturing Method)

The total components of the powders were mixed in a Henschel mixer and pulverized in a comminuting device. The resulting powders were transferred to the Henschel mixer and the total components of the oil phase were added to the powders. After agitation for eight minutes, the agitated product was taken out, pulverized by a comminuting device and put into a container to produce a caked eye shadow (product).

Example 10

Manufacture of Powder Foundation 2

Based on the composition of components, shown below, a powder foundation was prepared:

Composition of powder foundation

| components | weight parts |
|---|---|
| sericite | 17 |
| synthetic mica | 8 |
| plate-shaped talc | to 100 |
| silica-coated zinc oxide | 5 |
| complex material of Ex. 5 | 15 |

-continued

Composition of powder foundation

| components | weight parts |
|---|---|
| powders of spherical nylon | 5 |
| elastic powders of spherical nylon* | 15 |
| titanium oxide | 12 |
| iron oxide red | 0.8 |
| iron oxide yellow | 2 |
| iron oxide black | 0.1 |
| dimethyl polysiloxane | 3 |
| fluid paraffin | 5 |
| vaseline | 5 |
| sorbitan sesqui-isostearate | 1 |
| paraben | suitable amount |
| d-δ-tocopherol | suitable amount |
| perfume | suitable amount |

(Manufacturing Method)

The totality of the above components are comminuted and mixed together for a preset time in a mill containing a medium in the form of beads in alcohol. The so produced slurry was put into an inner saucer vessel and pressed, as alcohol was sucked, to prepare a powder foundation (product).

As for the elastic powders of spherical nylon, a product manufactured by Toray Dow Coning Silicone Inc. under the trade name of 'trefil' was used. The same applies for the following Examples.

Example 11

Production of Powder Foundation 3

A powder foundation was prepared based on the component composition shown below:

Composition of powder foundation

| components | weight parts |
|---|---|
| lecithin processed sericite | 23 |
| lecithin processed talc | 5 |
| lecithin processed synthetic mica | 10 |
| lecithin processed plate-like barium sulfate | to 100 |
| lecithin processed complex material of Ex. 3 | 12 |
| powders of spherical polymethyl sil sequioxane | 5 |
| elastic powders of spherical silicone | 10 |
| lecithin processed titanium oxide | 12 |
| lecithin processed iron oxide red | 0.8 |
| lecithin processed iron oxide yellow | 2 |
| lecithin processed iron oxide black | 0.1 |
| dimethyl polysiloxane | 3 |
| fluid paraffin | 5 |
| vaseline | 5 |
| sorbitan sequiisostearate | 1 |
| paraben | suitable amount |
| d-δ-tocopherol | suitable amount |
| perfume | suitable amount |

(Manufacturing Method)

The totality of the above components are comminuted and mixed together for a preset time in a mill containing a medium in the form of beads in alcohol. The so produced slurry was put into an inner saucer vessel and pressed, as alcohol was sucked, to prepare a powder foundation (product).

Example 12

Manufacture of Powder Foundation 4 (Manufacture of Powdered Solid Foundation for Summer Usable with Water)

A powder foundation was prepared based on the component composition shown below:

Composition of powder foundation

| | components | weight parts |
|---|---|---|
| powders | silicone processed sericite | 13 |
| | silicone processed synthetic mica | 7 |
| | silicone processed talc | to 100 |
| | silicone processed plate-shaped barium sulfate | 10 |
| | silicone processed complex substance of Ex. 3 | 12 |
| | powders of spherical polymethyl methacrylate powders | 5 |
| | elastic powders of spherical silicone | 2 |
| | elastic powders of spherical polyurethane | 3 |
| | aluminum stearate processed fine particles of titanium oxide | 6 |
| | silica coated zinc oxide | 4 |
| | silicone processed titanium oxide | 10 |
| | silicone processed iron oxide red | 1.2 |
| | silicone processed iron oxide yellow | 2.5 |
| | silicone processed iron oxide black | 0.9 |
| | parabene | suitable amount |
| oil phase | dimethyl polysiloxane | 4 |
| | methylphenyl polysiloxane | 3 |
| | octylmethoxy cinnamate | 3 |
| | polyether modified silicone | 2 |
| | d-δ-tocopherol | suitable amount |
| | perfume | suitable amount |

(Manufacturing Method)

The totality of the above components of the powders were mixed in a Henschel mixer and added to with an entire mixture of-oil phase components heated to 80° C. Using a spray nozzle, and agitated/mixed for ten minutes. The resulting mixture was taken out after spontaneous cooling to 40° C., and pulverized twice with a comminuting device to produce a powder foundation (product).

Example 13

Manufacture of Powder Foundation 5 (Manufacture of Powdered Solid Foundation for Summer Usable with Water)

A powder foundation was prepared based on the component composition shown below:

Composition of powder foundation

| | components | weight parts |
|---|---|---|
| powders | fluorine modified silicone processed synthetic mica | to 100 |
| | fluorine modified silicone processed talc | 13 |

-continued

Composition of powder foundation

| | components | weight parts |
|---|---|---|
| | fluorine modified silicone processed plate-shaped barium sulfate | 22 |
| | fluorine modified silicone processed complex substance of Ex. 3 | 13 |
| | powders of spherical nylon resin | 7 |
| | elastic powders of spherical silicone | 2 |
| | elastic powders of spherical polyurethane | 1 |
| | fluorine modified silicone processed fine particles of titanium oxide | 10 |
| | silicone processed titanium oxide | 9 |
| | silicone processed iron oxide red | 1.4 |
| | silicone processed iron oxide yellow | 2.8 |
| | silicone processed iron oxide black | 1.0 |
| | silica-coated zinc oxide | 5 |
| | paraben | suitable amount |
| oil phase | dimethyl polysiloxane | 4 |
| | methylphenyl polysiloxane | 1 |
| | octylmethoxy cinnamate | 3 |
| | polyether modified silicone | 2 |
| | vaseline | 1 |
| | d-δ-tocopherol | suitable amount |
| | perfume | suitable amount |

(Manufacturing Method)

The totality of the above components of the powders were mixed in a Henschel mixer and added to with an entire mixture of oil phase components heated to 80° C., using a spray nozzle, and agitated/mixed for ten minutes. The resulting mixture was taken out after spontaneous cooling to 40° C., and pulverized twice with a comminuting device to produce a powder foundation (product).

Example 14

Manufacture of Face Powders (White Powders)

Face powders were prepared based on the component composition shown below:

Composition of face powders

| | components | weight parts |
|---|---|---|
| powders | calcium stearate processed talc | to 100 |
| | powders of barium sulfate | 12 |
| | powders of porous silica | 10 |
| | powders of boron nitride | 3 |
| | powders of spherical titanium oxide | 5 |
| | complex substance of Ex. 5 | 7 |
| | silica-coated zinc oxide | 3 |
| | iron oxide red | 0.3 |
| | iron oxide yellow | 1.2 |
| | powders of spherical polymethyl syl sesquioxane | 8 |
| oil phase | vaseline | 1 |
| | squalane | 2 |
| | glycerol trioctanoate | 1 |
| | dimethyl polysiloxane | 1 |
| | paraben | suitable amount |
| | d-δ-tocopherol | suitable amount |
| | perfume | suitable amount |

(Manufacturing Method)

The totality of the above components of the powders were mixed in a Henschel mixer and added to with an entire mixture of oil phase components heated to 80° C. using a spray nozzle, and agitated/mixed for ten minutes. The resulting mixture was taken out after spontaneous cooling to 40° C., and pulverized twice with a comminuting device to produce face powders (product).

Example 15

Manufacture of W/O Emulsion Foundation

A W/O emulsion foundation was prepared based on the component composition shown below:

Composition of W/O emulsion foundation

| | components | weight parts |
|---|---|---|
| powders | silicone processed barium sulfate | 7 |
| | silicone processed complex substance of Ex. 3 | 4 |
| | silicone processed complex substance of Ex. 5 | 2 |
| | silicone processed titanium oxide | 12 |
| | silicone processed iron oxide red | 1.2 |
| | silicone processed iron oxide yellow | 2.6 |
| | silicone processed iron oxide black | 0.6 |
| | elastic powders of spherical silicone | 3 |
| | powders of spherical polymethyl methacrylate | 4 |
| | octylsilane processed fine particles of titanium oxide | 6 |
| | silica coated zinc oxide | 3 |
| | cyclomethicone | to 100 |
| Oil phase | dimethyl polysiloxane | 4 |
| | squalane | 3 |
| | polyether modified silicone | 2 |
| | sorbitan sesqui-isostearate | 1 |
| | distearyl chloride dimethylammonium | suitable amount |
| | d-δ-tocopherol | suitable amount |
| | perfume | suitable amount |
| aqueous phase | dipropylene glycol | 2 |
| | ion exchanged water | 20 |
| | Parabene | suitable amount |

(Manufacturing Method)

A mixture of powders and oil phase components was heated to 85° C. for dissolution and dispersion. To the resulting product was added an entire aqueous phase mixture which was separately prepared on heating to 85° C., and the resulting mass was emulsified at 85° C. On completion of emulsification, the emulsified product was cooled to room temperature and put into a container to prepare a liquid foundation (product).

Example 16

Manufacture of Ruth Powder (Face Powders)

Composition of ruth powder

| | Components | weight parts |
|---|---|---|
| powders | Talc | to 100 |
| | synthetic mica | 12 |
| | plate-shaped barium sulfate | 10 |
| | complex substance of Ex. 3 | 10 |
| | spherical porous silica powders | 4 |
| | spherical alumina powders | 4 |

-continued

| Composition of ruth powder | | |
|---|---|---|
| | Components | weight parts |
| oil phase | zinc flower | 3 |
| | silica-coated zinc oxide | 7 |
| | squalane | 3 |
| | paraben | suitable amount |
| | perfume | suitable amount |

(Manufacturing Method)

The totality of the above components of the powders were mixed in a Henschel mixer and added to with an entire mixture of oil phase components heated to 80° C., using a spray nozzle, and agitated/mixed for ten minutes. The resulting mixture was taken out after spontaneous cooling to room temperature, and pulverized twice with a comminuting device to produce ruth powders (product).

Example 17

Manufacture of W/O Emulsion Foundation 2

A W/O emulsion foundation was prepared based on the component composition shown below:

| Composition of W/O emulsion foundation | | |
|---|---|---|
| | components | weight parts |
| Powders | fluorine modified silicone processed mica | 5 |
| | fluorine modified silicone processed sericite | 7 |
| | fluorine modified silicone processed titanium oxide | 12 |
| | fluorine modified silicone processed iron oxide | 4 |
| | fluorine modified silicone processed complex substance of Ex. 3 | 6 |
| | octylsilane processed fine particles of titanium oxide | 4 |
| | powders of spherical polymethyl methacrylate | 5 |
| | elastic powders of spherical silicone | 5 |
| | silica coated zinc oxide | 4 |
| oil phase | cyclomethicone | to 100 |
| | dimethyl polysiloxane | 4 |
| | squalane | 3 |
| | polyether modified silicone | 1 |
| | fluorine modified polyether modified silicone | 3 |
| | distearyl chloride dimethyl ammonium | suitable amount |
| | d-δ-tocopherol | suitable amount |
| | perfume | suitable amount |
| aqueous phase | dipropylene glycol | 2 |
| | ion exchanged water | 20 |
| | paraben | suitable amount |

(Manufacturing Method)

A mixture of powders and oil phase components was heated to 85° C. for dissolution and dispersion. To the resulting product was added an entire aqueous phase mixture, which was previously separately prepared on heating to 85° C., and the resulting mass was emulsified at 85° C. On completion of emulsification, the emulsified product was cooled to room temperature and put into a container to prepare a liquid foundation (product).

Example 18

Evaluation of Cosmetics

The respective formulations were evaluated by eight expert panelists, in contrast to commercially available products and products of the Comparative Examples.

Figure 4:
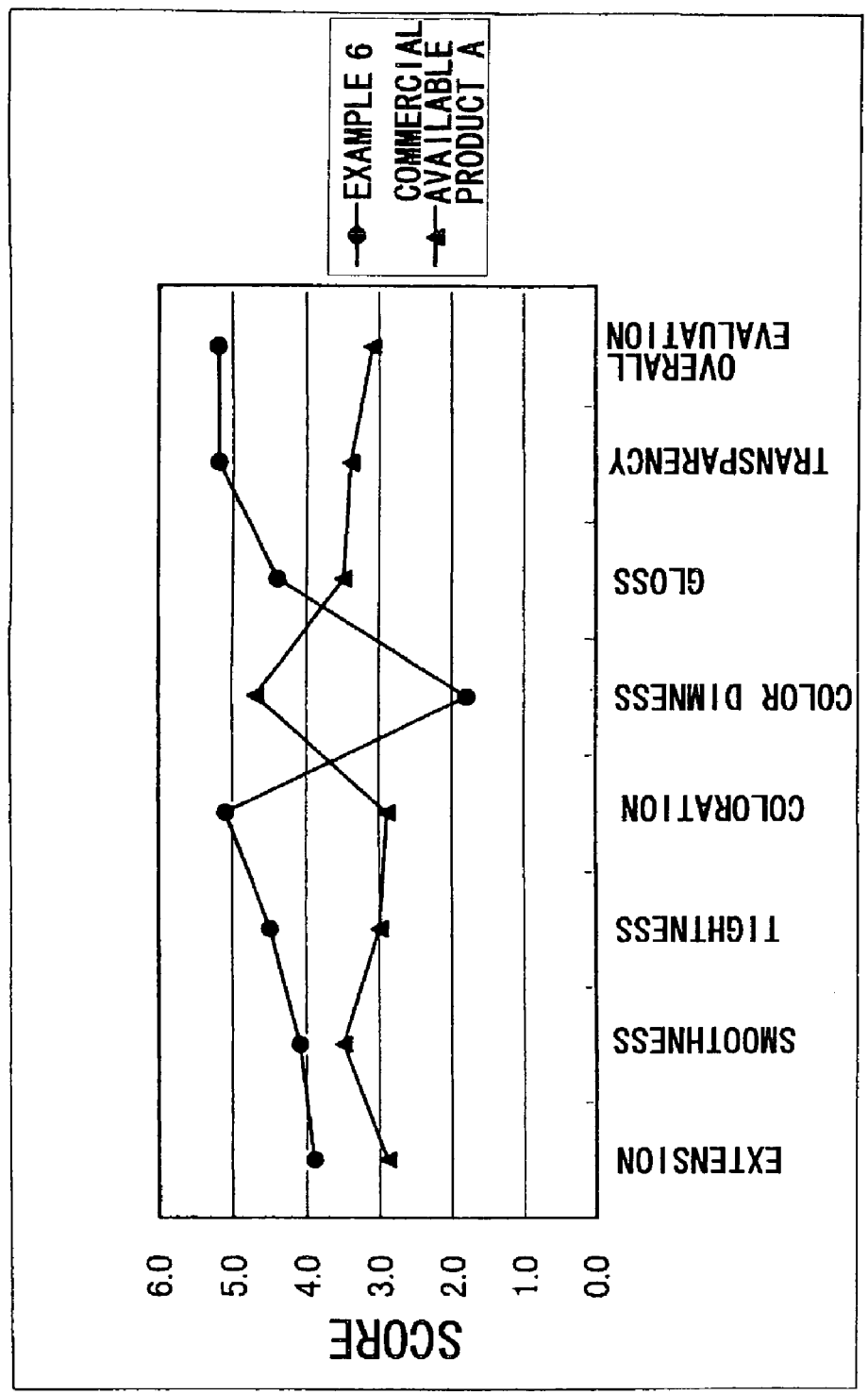
FIG. 4 shows the results of evaluation on lipstick in Example 18 where ● and ▲ denote an inventive product (Example 6) and a commercially available product A, respectively.
Figure 5:
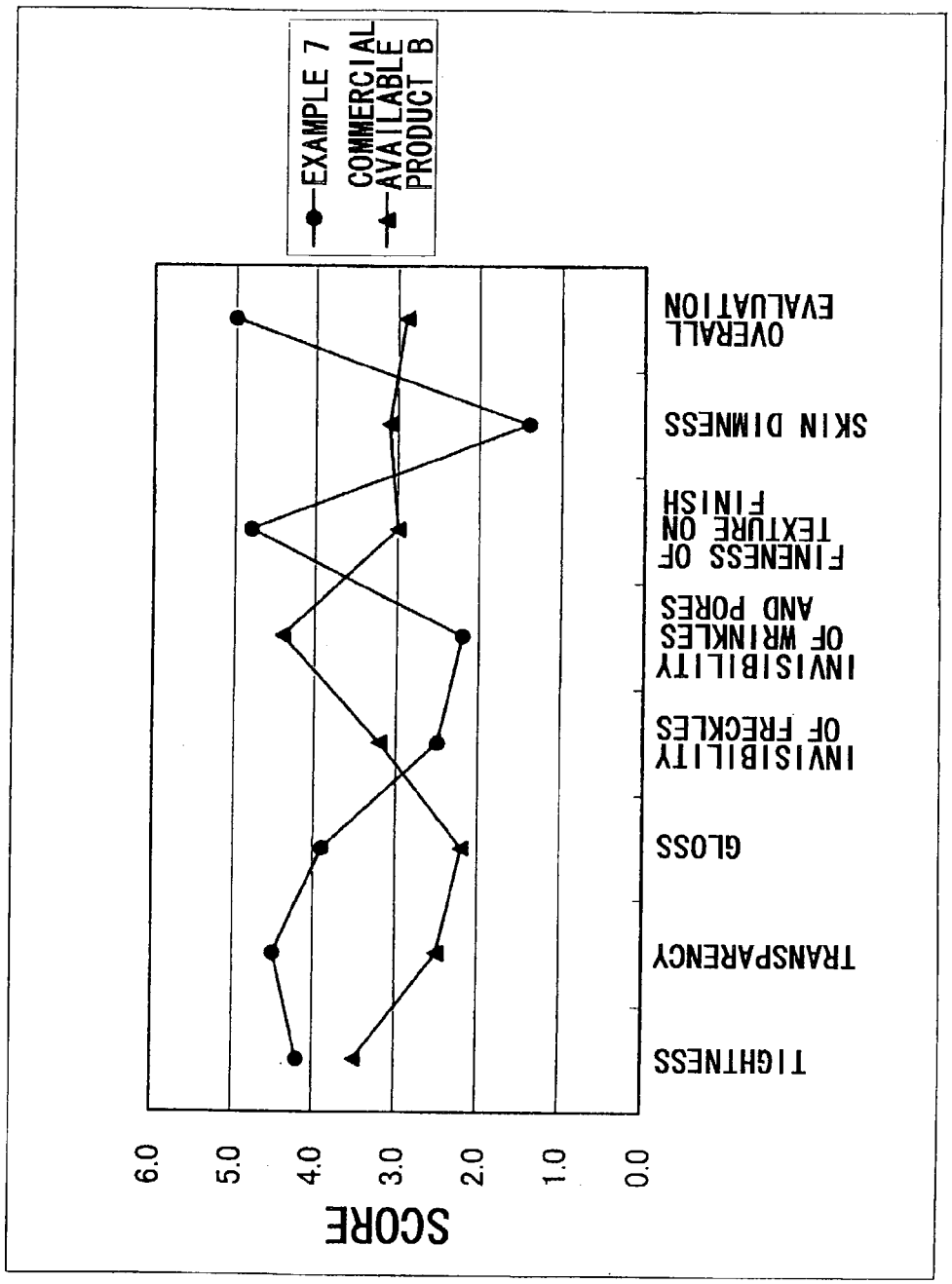
FIG. 5 shows the results of evaluation on a cream foundation in Example 18 where ● and ▲ denote those for an inventive product (Example 7) and those for a commercially available product B, respectively.
Figure 6:
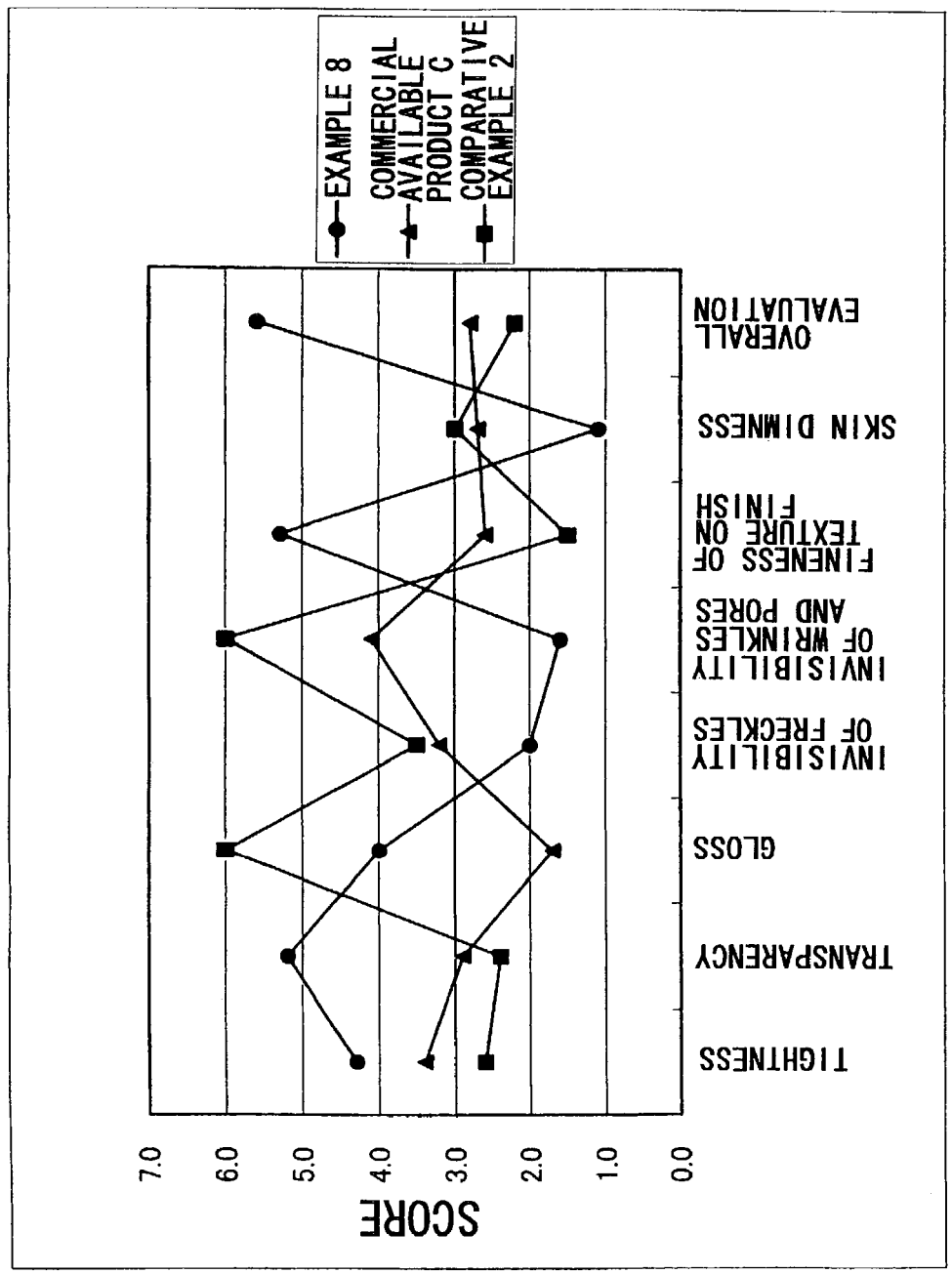
FIG. 6 shows the results of evaluation on a powder foundation in Example 18, where ●, ▲ and ■ denote an inventive product (Example 8), a commercially available product C and the Comparative Example 2, respectively.
Figure 7:
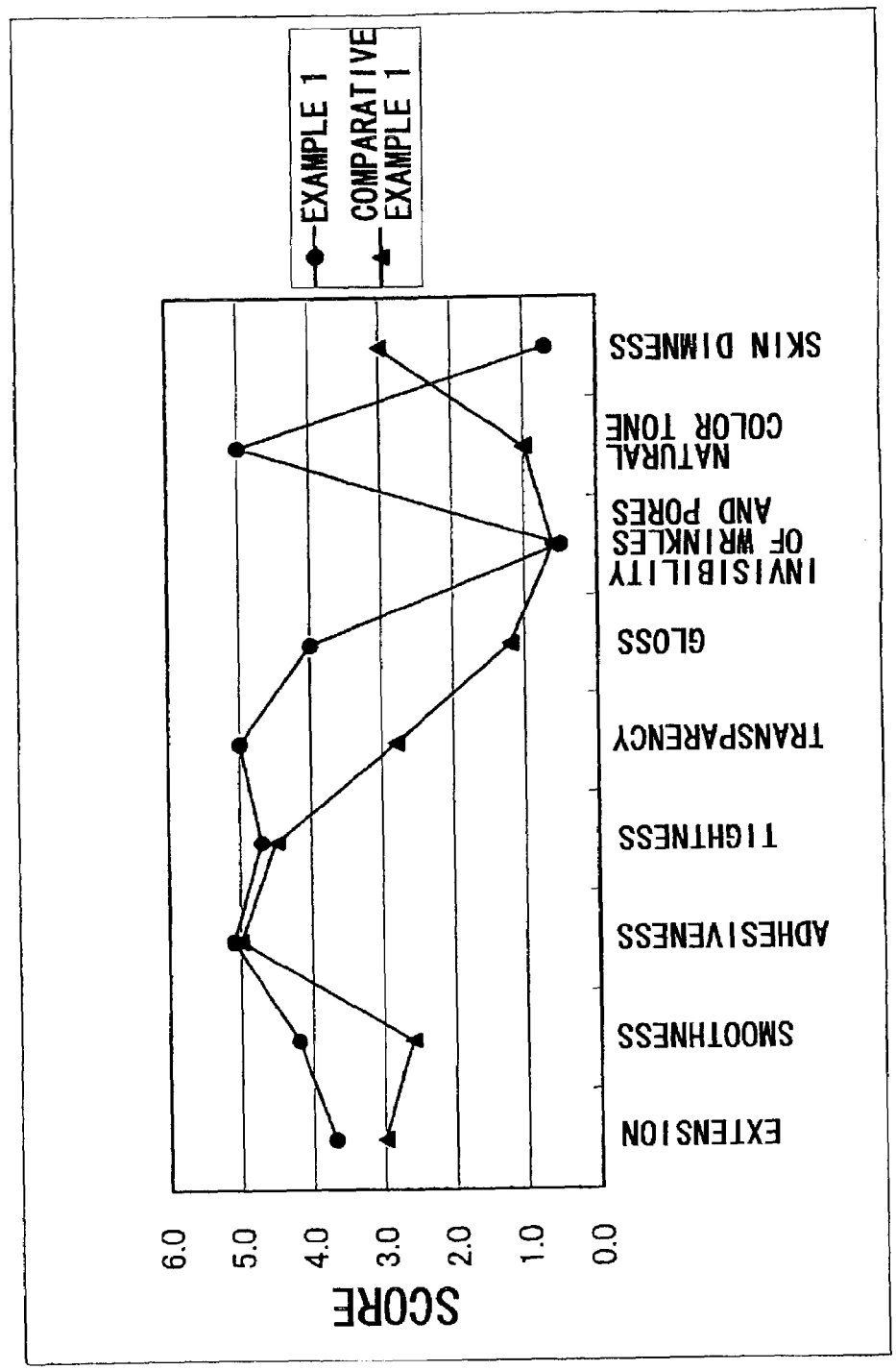
FIG. 7 shows the results of evaluation of the effect of the composite powder itself in Example 18, where ● and ▲ denote an inventive product (Example 1) and the Comparative Example 1, respectively.

For respective samples (Examples 1 and 6 to 8), functional evaluation was conducted as follows: The results for the lipstick are shown in FIG. 4 (comparison of Example 6 and the commercially available product A), while those for the cream foundation are shown in FIG. 5 (comparison of Example 7 and the commercially available product B)and those for the powder foundation are shown in FIG. 6 (comparison of Example 8 to the commercially available product C and the Comparative Example 2). The results for the evaluation of the effect of the powders are shown in FIG. 7 (comparison of Example 1 to the Comparative Example 1).

As the criteria for evaluation, seven stage evaluation of "none", "extremely slight", "slight", "relatively high", "appreciably high", "extremely high" and "drastically high" was used.

| (For cream foundation and powder foundation) | |
|---|---|
| tightness | none (0 point) to drastic (6 points) |
| transparency | none (0 point) to drastic (6 points) |
| gloss | none (0 point) to drastic (6 points) |
| invisibility of freckles | none (0 point) to drastic (6 points) |
| invisibility of wrinkles and pores | none (0 point) to drastic (6 points) |
| fineness of texture on finish | extremely rough (0 point) to drastically fine (6 points) |
| skin dimness | none (0 point) to drastic (6 points) |
| overall evaluation | worst (0 point) to extremely good (6 points) |
| (For lipstick) | |
| extension | none (0 point) to drastic (6 points) |
| smoothness | none (0 point) to drastic (6 points) |
| tightness | none (0 point) to drastic (6 points) |
| coloration | none (0 point) to drastic (6 points) |
| color dimness | none (0 point) to drastic (6 points) |
| gloss | none (0 point) to drastic (6 points) |
| transparency | none (0 point) to drastic (6 points) |
| overall evaluation | worst (0 point) to extremely good (6 points) |
| (For evaluation of composite powders) | |
| extension | none (0 point) to drastic (6 points) |
| smoothness | none (0 point) to drastic (6 points) |
| adhesiveness | none (0 point) to drastic (6 points) |
| tightness | none (0 point) to drastic (6 points) |
| transparency | none (0 point) to drastic (6 points) |
| gloss | none (0 point) to drastic (6 points) |
| invisibility of wrinkles and pores | none (0 point) to drastic (6 points) |
| natural color tone | none (0 point) to drastic (6 points) |
| skin dimness | none (0 point) to drastic (6 points) |

Meanwhile, in evaluating the Example 1, the product was directly coated on the skin using a puff for comparison with the product of the Comparative Example 1.

FIG. 4 shows the results of comparison of the lipstick of Example 6 with the commercially available product A. The inventive product suffered from only little color dimness or from excessive gloss, such that it demonstrated favorable results when compared with the commercial product in any items and extremely favorable results as to overall evaluation. FIG. 5 shows the results of comparison of the Example 7 with the commercially available product B. The results indicate that the inventive product is extremely superior as is the case of the results of evaluation of FIG. 4. FIG. 6 shows the results of comparison of the Example 8 as to the powder foundation with the commercially available product C and with the Comparative Example 2. The results indicate that the inventive product is extremely superior. It is noted that neither "excessive" gloss (Comparative Example 2) nor only poor gloss (commercially available product C) is desirable. The moderate gloss as the inventive product is desirable.

It may be seen from the above results that the inventive products are appreciably superior to the commercially available products or to products of the Comparative Examples in any items of evaluation or in the overall evaluation.

Meritorious Effect of the Invention

The composite powders of the present invention are free of dimness caused by changes with time of a cosmetic film as compared to a conventional product, while being superior in a feeling of "elasticity" and transparency, in addition to exhibiting the correcting effect of the troubled morphology of the skin, such as wrinkles, pore openings, hard texture of the skin, when the powders are used as cosmetics. The present invention is, therefore, extremely useful; in particular in the field of cosmetics.

By surface treatment for cosmetic powders on the surface of the composite powder, desirably surface processing with silicone, amino acids, lecithin or fluorine compounds, the meritorious effects can be improved further.

The invention claimed is:

1. A composite powder for cosmetics comprising a powdery base and aluminum hydroxide adhered to at least a portion of the outer surface of said base, wherein said aluminum hydroxide is comprised of a formation of spherically shaped particles and mesh formation of string shaped particles, and wherein said base is a complex material comprising a particle of powder selected from the group consisting of clay mineral, barium sulfate, alumina, silica and magnesium fluoride, and a coating on said particle of powder, said coating comprising at least one selected from the group consisting of titanium oxide, basic lead carbonate, bismuth oxychloride, cadmium oxide, zirconium oxide, tin oxide, silver and gold, wherein said spherically-shaped formation contained in the adhered aluminum hydroxide comprises any one of spheres, ellipsoids, disc spheres, spindle-shaped spheres and combinations thereof in the planar and/or vertical direction, wherein the length of a mesh forming the mesh formation of aluminum hydroxide is about 300 nm at the longest, with the thickness (diameter) of a string of the mesh forming the mesh formation being about 5 to 30 nm;

wherein 2 to 75 weight % of aluminum hydroxide is present in a total weight of the adhered aluminum hydroxide and the base.

2. The composite powder of claim 1, wherein said mesh formation contained in the adhered aluminum hydroxide comprises two-dimensional and/or three-dimensional formation(s) of aluminum hydroxide.

3. The composite powder of claim 1, wherein the mesh formation is present on or above the surface of said spherically-shaped formation of aluminum hydroxide.

4. The composite powder of claim 1, wherein the average particle size of the coated particle of said complex material is 2 to 500 nm.

5. The composite powder of claim 1, wherein the diameter of said sphere is 0.1 to 10 μm, and the long and short diameters of said ellipsoid being 0.4 to 2 μm and 0.2 to 1.5 μm, respectively.

6. The composite powder of claim 1, wherein said base further comprises a color tint component.

7. The composite powder of claim 6, wherein said color tint component is any one of ferric oxide, triiron tetraoxide, iron oxide hydrate, cobalt oxide, cobalt phosphate, chromium oxide, chromium hydroxide, ultramarine, Prussian blue and Red 226.

8. The composite powder of claim 1, wherein the shape of said base comprises any one of a scale shape and a platy shape.

9. Cosmetics comprising the composite powder of claim 1.

10. The cosmetics of claim 9, wherein said composite powder is comprised in an amount of 1 to 100 weight %.

11. The composite powder of claim 1, wherein said composite powder comprises at least 10 weight % of said adhered aluminum hydroxide in a total weight of said base and said aluminum hydroxide.

12. The composite powder of claim 1, wherein said particle of powder of said base is pearl pigment.

13. The composite powder of claim 1, wherein said particle of powder of said base is iris foliate pearl pigment.

14. The composite powder of claim 1, wherein said particle of powder of said base is titanium mica.

* * * * *